US009642899B2

(12) United States Patent
McGregor et al.

(10) Patent No.: US 9,642,899 B2
(45) Date of Patent: May 9, 2017

(54) IMPLANTATION OF A CARDIAC XENOGRAFT FROM A B4GALNT2KO AND GTKO TRANSGENIC PIG TO REDUCE IMMUNOGENICITY

(75) Inventors: Christopher G. A. McGregor, Rochester, MN (US); Guerard W. Byrne, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 841 days.

(21) Appl. No.: 13/696,478

(22) PCT Filed: Apr. 11, 2011

(86) PCT No.: PCT/US2011/031976
§ 371 (c)(1),
(2), (4) Date: Jan. 17, 2013

(87) PCT Pub. No.: WO2011/139488
PCT Pub. Date: Nov. 10, 2011

(65) Prior Publication Data
US 2013/0111614 A1    May 2, 2013

Related U.S. Application Data

(60) Provisional application No. 61/332,127, filed on May 6, 2010.

(51) Int. Cl.
| A01K 67/027 | (2006.01) |
| C12N 15/00 | (2006.01) |
| A61K 39/00 | (2006.01) |
| A61K 35/34 | (2015.01) |
| C12N 15/85 | (2006.01) |
| A61K 38/00 | (2006.01) |

(52) U.S. Cl.
CPC ........ *A61K 39/001* (2013.01); *A01K 67/0276* (2013.01); *A61K 35/34* (2013.01); *C12N 15/8509* (2013.01); *A01K 2207/30* (2013.01); *A01K 2227/108* (2013.01); *A01K 2267/02* (2013.01); *A01K 2267/025* (2013.01); *A61K 38/00* (2013.01)

(58) Field of Classification Search
CPC ........ A61K 35/34; A61K 38/00; A61K 38/11; A61K 39/001; A01K 2207/30; A01K 67/0276
See application file for complete search history.

(56) References Cited

U.S. PATENT DOCUMENTS

| 4,106,129 A | 8/1978 | Carpentier et al. |
| 4,865,600 A | 9/1989 | Carpentier et al. |
| 5,633,076 A | 5/1997 | DeBoer et al. |
| 5,821,117 A | 10/1998 | Sandrin et al. |
| 6,210,957 B1 | 4/2001 | Carpentier et al. |
| 6,338,740 B1 | 1/2002 | Carpentier |
| 6,455,037 B1 | 9/2002 | Ioannou et al. |
| 6,547,827 B2 | 4/2003 | Carpentier et al. |
| 6,558,418 B2 | 5/2003 | Carpentier et al. |
| 6,561,970 B1 | 5/2003 | Carpentier et al. |
| 6,572,867 B1 | 6/2003 | Schwarz et al. |
| 6,849,448 B1 | 2/2005 | D'Apice et al. |
| 6,878,168 B2 | 4/2005 | Carpentier et al. |
| 7,037,333 B2 | 5/2006 | Myers et al. |
| 9,006,510 B2 | 4/2015 | Byrne et al. |
| 2002/0187132 A1 | 12/2002 | Mcgregor et al. |
| 2004/0141944 A1 | 7/2004 | Schwarz et al. |
| 2004/0171155 A1 | 9/2004 | D'Apice et al. |
| 2008/0124396 A1 | 5/2008 | Schwarz et al. |
| 2009/0043383 A1 | 2/2009 | McGregor et al. |
| 2009/0324674 A1 | 12/2009 | Burne et al. |

FOREIGN PATENT DOCUMENTS

| WO | WO 94/06903 | 3/1994 |
| WO | WO 94/21799 | 9/1994 |
| WO | WO 2005/094587 | 10/2005 |

OTHER PUBLICATIONS

Diamond et al (Transplantation. 2001, 71(1):132-42).*
Byrne et al (Xenotransplantation, 21: 543-554, 2014).*
Cowan et al, (Curr Opin Organ Transplant; 16(2): 214-221, 2011).*
Estrada et al., "Evaluation of human and non-human primate antibody binding to pig cells lacking GGTA1/CMAH/β4GalNT2 genes," Xenotransplantation, doi: 10.1111/xen.12161, Epub Mar. 1, 2015.
Bartek et al., "Frame-mounted tissue heart valves: technique of construction," *Thorax*, 29:51-55, 1974.
Bovin et al., "Repertoire of human natural anti-glycan immunoglobulins. Do we have auto-antibodies?" *Biochim Biophys Acta.*, 1820(9):1373-1382, Epub Feb. 21, 2012.
Cooper et al., "Oligosaccharides and discordant xenotransplantation," *Immunol Rev.*, 141:31-58, Oct. 1994.

(Continued)

*Primary Examiner* — Anoop Singh
*Assistant Examiner* — Magdalene Sgagias
(74) *Attorney, Agent, or Firm* — Fish & Richardson P.C.

(57) ABSTRACT

This document provides methods and materials involved in reducing cardiac xenograft rejection. For example, methods and materials for preparing transgenic pigs expressing reduced or no endogenous $Sd^a$ or SDa-like glycans derived from the porcine β1,4 N-acetyl-galactosaminyl transferase 2 (B4GALNT2) glycosyltransferase and/or reduced or no endogenous α-Gal antigens, methods and materials for modifying the xenograft recipient's immunological response to non-Gal antigens (e.g. CD46, CD59, CD9, PROCR, and ANXA2) to reduce cardiac xenograft rejection, and methods and materials for monitoring the progress of xenotransplant immunologic rejection are provided.

3 Claims, 17 Drawing Sheets

(56) References Cited

OTHER PUBLICATIONS

Diswall et al., "Structural characterization of alpha1,3-galactosyltransferase knockout pig heart and kidney glycolipids and their reactivity with human and baboon antibodies," *Xenotransplantation*, 17(1):48-60, Jan.-Feb. 2010.
Diswall et al., "Studies on glycolipid antigens in small intestine and pancreas from alpha1,3-galactosyltransferase knockout miniature swine," *Transplantation*, 84(10):1348-1356, Nov. 27, 2007.
Huflejt et al., "Anti-carbohydrate antibodies of normal sera: findings, surprises and challenges," *Mol Immunol.*, 46(15):3037-3049, Epub Jul. 15, 2009.
Lila et al., "Gal knockout pig pericardium: new source of material for heart valve bioprostheses," *J Heart Lung Transplant.*, 29(5):538-543. Epub Dec. 29, 2009.
McGregor et al., "Cardiac xenotransplantation technology provides materials for improved bioprosthetic heart valves," *J Thorac Cardiovasc Surg.*, 141(1):269-275, Jan. 2011.
McGregor et al., "Human CD55 expression blocks hyperacute rejectoin and restricts complement activation in Gal knockout cardiac xenografts," *Transplantation*, 93(7):686-692, Apr. 15, 2012.
Miyagawa et al., "Survey of glycoantigens in cells from α1-3galactosyltransferase knockout pig using a lectin microarray," *Xenotransplantation*, 17(1):61-70, Jan.-Feb. 2010.
Mohiuddin et al., "B-cell depletion extends the survival of GTKO. hCD46Tg pig heart xenografts in baboons for up to 8 months," *Am J Transplant.*, 12(3):763-71. Epub Nov. 9, 2011.
Mohiuddin et al., "One-year heterotopic cardiac xenograft survival in a pig to baboon model," *Am J Transplant.*, 14(2):488-489, Epub Dec. 11, 2013.
Simionescu, "Prevention of calcification in bioprosthetic heart valves: challenges and perspectives," *Expert Opin Biol Ther.*, 4(12):1971-1985, Dec. 2004.
Yeh et al., "Investigation of potential carbohydrate antigen targets for human and baboon antibodies," *Xenotransplantation*, 17(3):197-206, May-Jun. 2010.
Zilla et al., "Prosthetic heart valves: Catering for the few," *Biomaterials*, 29(4):385-406. Epub Oct. 24, 2007
"Edwards Launches New Mitral Magna Heart Valve in Europe," 2005, Edwards Lifesciences Corporation, News Release.
Adams et al. "Human membrane cofactor protein (MCP, CD 46) protects transgenic pig hearts from hyperacute rejection in primates", Xenotransplantation. Feb. 2001, vol. 8, Issue 1, pp. 36-40.
Arat et al., "In Vitro Development of Bovine Nuclear Transfer Embryos from Transgenic Clonal Lines of Adult and Fetal Fibroblast Cells of the Same Genotype," *Biol. Redprod.*, 2002, 66(6):1768-1774.
Arat et al., "Production of transgenic bovine embryos by transfer of transfected granulosa cells into enucleated oocytes," *Mol. Reprod. Dev.*, 2001, 60:20-26.
Azimzadeh et al. "Xenograft rejection: molecular mechanisms and therapeutic prospects", Hematology and Cell Therapy 1997, 38(4):331-343.
Bracy et al "Inhibition ofxenoreactive natural antibody production by retroviral gene therapy", Science 1998, 281: 1845-1847.
Byrne et al. "Protection of xenogeneic cardiac endothelium from human complement by expression of CD59 or DAF in transgenic mice", Transplantation 1995,60(10):1149-1156.
Byrne et al. "Proteomic identification of non-Gal antibody targets after pig-to-primate cardiac xenotransplantation", Xenotransplantation 2008, 15:268-276.
Byrne et al. "Transgenic pigs expressing human CD59 and decay-accelerating factor produce an intrinsic barrier to complement-mediated damage", Transplantation 1997,63(1):149-155.
Cesarman-Maus et al. "Autoantibodies against the fibrinolytic receptor, annexin 2, in antiphospholipid syndrome", Blood 2006, 107(11):4375-4382.
Cockrell et al. "Annexin A2: biology and relevance to the antiphospholipid syndrome", Lupus 2008, 17(10):943-951.

Cooper et al. "Alpha1,3-galactosyltransferase gene-knockout pigs for xenotransplantation: where do we go from here?" Transplantation 2007, 84(1):1-7.
Cooper, "Clinical xenotransplantation-how close are we?" *The Lancet*, 2003, 362(9383):557-559.
Cozzi et al. "Characterization of pigs transgenic for human decay-accelerating factor", Transplantation 1997, 64(10): 1383-1392.
Davila et al. "T-cell responses during pig-to-primate xenotransplantation", Xenotransplantation 2006, 13(1):31-40.
Diamond et al. "A human CD46 transgenic pig model system for the study of discordant xenotransplantation", Transplantation 2001, 71(1): 132-142.
Esmon, C.T. "Structure and functions of the endothelial cell protein C receptor", Crit Care Med 2004,32(5 Suppl):5298-301.
Fischer-Lougheed et a. "Gene therapy to inhibit xenoantibody production using lentiviral vectors in non-human primates", Gene Ther 2007,14(1):49-57.
Geisel et al., "In vivo Activity of Released cell Wall Lipids of Mycobacterium Bovis Bacillus Calmette-Guerin is Due Principally to Trehalose Mycolates," *J. Immunol.*, 2005, 174(8):5007-5015.
Genbank Accession No. J04989, dated Apr. 27, 1993, 3 pages.
Genbank Accession No. NM_177511, dated Jun. 3, 2007, 3 pages.
Genbank Accession No. NW_928396, dated Sep. 30, 2005, 3 pages.
Genbank Accession No. XM_605800, dated Sep. 30, 2005, 3 pages.
Gould and Auchincloss. "Direct and indirect recognition: the role of MHC antigens in graft rejection", Immunology Today 20(2):77-82, 1999.
Harris et al. "Human and rodent decay-accelerating factors (CD55) are not species restricted in their complement-inhibiting activities", Immunology 2000, 100(4):462-470.
International Preliminary Report on Patentability for Application No. PCT/US2011/031976, dated Nov. 6, 2012, 6 pages.
International Search Report and Written Opinion for Application No. PCT/US2011/031976, dated Jan. 2, 2012, 11 pages.
Johnson et al. "Cultivation and characterization of coronary microvascular endothelial cells: a novel porcine model using micropigs", Microvascular research 2002, 64(2):278-288.
Kagan et al. "Expression of complement regulatory factors using heterologous promoters in transgenic mice", Transplant Proc 1994,26(3):1242.
Kamada et al. "Structural studies on a binding site for Dolichos biflorus agglutinin in the small intestine of the mouse", J Biochem 1991, 109(1):178-183.
Kawakatsu et al. "Antithrombotic effect of an anti-glycoprotein IIB/IIIA antibody in primate lethal thrombosis", Thromb Res 1993, 70(3):245-254.
Lerino et al. "Transfer of swine major histocompatibility complex class II genes into autologuous bone marrow cells of baboons for the induction of tolerance across xenogeneic barriers", Transplantation 1999,67(8):1119-1128.
Li et al. "The DXD motif is required for GM2 synthase activity but is not critical for nucleotide binding", Glycobiology 2001, 11:217-229.
Liszewski et al. "Membrane cofactor protein (MCP or CD46): Newest member ofthe regulators of complement activation gene cluster", Annu Rev Immuno11991, 9:431-455.
Malagolini et al. "Identification and characterization of the Sda beta 1,4,N-acetylgalactosaminyltransferase from pig large intestine", Glycoconj J 1994, 11(2):89-95.
McKenzie et al., "Strategies to Overcome the Anti-Galα(1-3)Gal Reaction in Xenotransplantation," *Transplantation Proceedings*, 1996, 28(2):537.
Meri et al. "Human protectin (CD59), an 18,000-20,000 MW complement lysis restricting factor, inhibits C5b-8 catalysed insertion of C9 into lipid bilayers", Immunology 1990, 71: 1-9.
Montiel et al. "Molecular cloning, gene organization and expression of the human UDP-GaINAc:Neu5Acalpha2-3Galbeta-R beta1,4-N-acetylgalactosaminyltransferase responsible for the biosynthesis of the blood group SdalCad antigen: evidence for an unusual extended cytoplasmic domain", The Biochemical journal 2003, 373(Pt 2):369-379.

(56) References Cited

OTHER PUBLICATIONS

Morelli and Thomson "Tolerogenic dendritic cells and the quest for transplant tolerance", Nat Rev Immunol 2007, 7(8):610-621.

Morgan et al. "Homologous restriction in complement lysis: roles of membrane complement regulators", Xenotransplantation 2005, 12(4):258-265.

Nottle et al., "Production of homozygous α-1,3-galactosyltransferase knockout pigs by breeding and somatic cell nuclear transfer", Xenotransplantation 2007, 14(4): 339-344.

Paulson et al., Sweet spots in functional glycomics, Nature Chem. Biol. 2006, 2(5):238-248.

Phelps et al., "Production of aα1,3-Galactosyltransferase-Deficient Pigs," *Science*, 2003, 299(5605):411-414.

Piller et al. "Comparison of the carbohydrate-binding specificities of seven Nacetyl-D-galactosamine-recognizing lectins", European journal of biochemistry 1990, 191(2):461-466.

Rescher and Gerke. "Annexins-unique membrane binding proteins with diverse functions", J Cell Sci 2004, 117(Pt 13):2631-2639.

Reznicek et al. "A hemolytic reaction implicating Sda antibody missed by immediate spin crossmatch", Vox Sang 1992, 62(3):173-175.

Rhoades et al., "Cell wall lipids from *Mycobacterium bovis* BCG are inflammatory when inoculated within a gel matrix: Characterization of a new model of the granulomatous response to mycobacterial components," *Tuberculosis*, 2005, 85(3):159-176.

Sendai et al., "Heterozygous disruption of the α1,3-galactosyltransferase gene in cattle," *Transplantation*, 2003, 76(6):900-902.

Sendai et al., "α1,3-Galactosyltransferase-Gene Knockout in Cattle using a Single Targeting Vector with loxP Sequences and Cre-Expressing Adenovirus," *Transplantation*, 2006, 81(5):760-766.

Shah et al., "Active site studies of bovine alpha1-3galactosyltransferase and its secondary structure prediction," *Biochem. Biophys. Acta.*, 2000, 1480:222-234.

Sharma et al., "Pig cells that lack the gene for alpha1,3-galactosyltransferase express low levels of the gal antigen", Transplantation 2003, 75:430-436.

Smith and Lowe. "Molecular cloning of a murine N-acetylgalactosamine transferase cDNA that determines expression of the T lymphocyte-specific CT oligosaccharide differentiation antigen", J Biol Chem 1994, 269(21): 15162-15171.

Solanes et al. "Histological basis of the porcine femoral artery for vascular research", Anatomia, histologia, embryologia 2005, 34(2):105-111.

Sonntag et al. "Tolerance to solid organ transplants through transfer of MHC class II genes", The Journal of Clinical Investigation 2001,107(1):65-71.

Spitalnik et al. "The serology of Sda effects of transfusion and pregnancy", Vox Sang 1982,42(6):308-312.

Tearle et al., "The α-1,3-galactosyltransferase knockout mouse. Implications for xenotransplantation," *Transplantation*, 1996, 61(1):13-19.

Tormey et al. "Red blood cell alloantibody frequency, specificity, and properties in a population of male military veterans", Transfusion 2008, 48(10):2069-2076.

Van de Wouwer et al. "Thrombomodulin-protein C-EPCR system: integrated to regulate coagulation and inflammation", Arterioscler Thromb Vase Bioi 2004, 24(8): 1374-1383.

Van den Berg and Morgan. "Complement-inhibiting activities of human CD59 and analogues from rat, sheep, and pig are not homologously restricted", J Immunol 1994, 152(8):4095-4101.

Vanhove et al. "Intracellular expression in pig cells of anti-α1,3galactosyltransferase single-chain fv antibodies reduces galα1,3gal expression and inhibits cytotoxicity mediated by anti-gal xenoantibodies," *Transplantation*, 1998, 66(11):1477-1485.

WIPO Authorized Officer Ellen Moyse, International Preliminary Report on Patentability, PCT/US2007/071007 mailed Jan. 15, 2009, 9 pages.

WIPO Authorized Officer Kee Yeun Kim, International Search Report/Written Opinion, PCT/US2007/071007 mailed Nov. 7, 2007, 15 pages.

Wong et al. "Glycan arrays: biological and medical applications", Curro Opin. Chem. Biol. 2008, 12:86-92.

Ye et al. "The endothelial cell protein C receptor (EPCR) functions as a primary receptor for protein C activation on endothelial cells in arteries, veins, and capillaries", Bioehem Biophys Res Commun 1999,259(3):671-677.

Abicht et al., "Pre-clinical heterotopic intrathoracic heart xenotransplantation: a possibly useful clinical technique," *Xenotransplantation*, 22(6):427-442, Epub Nov. 25, 2015.

Azimzadeh et al., "Development of a consensus protocol to quantify primate anti-non-Gal xenoreactive antibodies using pig aortic endothelial cells," Xenotransplantation, 21(6):555-566, Epub Sep. 1, 2014.

Bush et al., "Coagulopathy in α-galactosyl transferase knockout pulmonary xenotransplants," Xenotransplantation, 18(1):6-13, Jan.-Feb. 2011.

Byrne et al., "Changes in cardiac gene expression after pig-to-primate orthotopic xenotransplantation," Xenotransplantation, 18(1):14-27, Jan.-Feb. 2011.

Byrne et al., "Cloning and expression of porcine β1,4 N-acetylgalactosaminyl transferase encoding a new xenoreactive antigen," *Xenotransplantation*, 21(6):543-554, Epub Sep. 1, 2014.

Byrne et al., "Evaluation of different alpha-Galactosyl glycocogjugates for use in xenotransplantation," Bioconjug Chem., 13(3):571-581, May-Jun. 2002.

Byrne et al., "First quantification of alpha-Gal epitope in current glutaraldehyde-fixed heart valve bioprosthesis (by Naso et al.)," Xenotransplantation, 21(1):11-12, Epub Nov. 5, 2013.

Byrne et al., "Histopathologic insights into the mechanism of anti-non-Gal antibody-mediated pig cardiac xenograft rejection," Xenotransplantation, 20(5):292-307, Sep.-Oct. 2013.

Byrne et al., "Identification of new carbohydrate and membrane protein antigens in cardiac xenotransplantation," Transplantation, 91(3):287-292, Feb. 15, 2011.

Byrne et al., "Increased immunosuppression, not anticoagulation, extends cardiac xenograft survival," *Transplantation*, 82(12):1787-1791, Dec. 27, 2006.

Byrne et al., "Proteomic identification of non-Gal antibody targets after pig-to-primate cardiac xenotransplantation," Xenotransplantation, 15(4):268-276, Jul.-Aug. 2008.

Byrne et al., "Recent investigations into pig antigen and anti-pig antibody expression," Int J Surg., 23(Pt B):223-228, Epub Aug. 22, 2015.

Byrne et al., "Warfarin or low-molecular-weight heparin therapy does not prolong pig-to-primate cardiac xenograft function," *Am J Transplant*, 5(5):1011-1020, May 2005.

Byrne et al., "Cardiac xenotransplantation: progress and challenges," Curr Opin Organ Transplant., 17(2):148-154, Apr. 2012.

Davila et al., "T-cell responses during pig-to-primate xenotransplantation," Xenotransplantation, 13(1):31-40, Jan. 2006.

Diamond et al., "Analysis of the control of the anti-gal immune response in a non-human primate by galactose alpha1-3 galactose trisaccharide-polyethylene glycol conjugate," Transplantation, 73(11):1780-1787, Jun. 15, 2002.

Khalpey et al., "Mammalian mismatches in nucleotide metabolism: implications for xenotransplantation," *Mol Cell Biochem.*, 304(1-2):109-117, Epub Jul. 27, 2007.

Lin et al., "A pig-to-mouse coronary artery transplantation model for investigating the pathogenicity of anti-pig antibody," Xenotransplantation, 22(6):458-467, Epub Oct. 22, 2015.

McGregor et al., "Cardiac xenotransplantation technology provides materials for improved bioprosthetic heart valves," *J Thorac Cardiovasc Surg.*, 141(1):269-75, Jan. 2011.

McGregor et al., "Cardiac xenotransplantation: progress toward the clinic," Transplantation, 78(11):1569-1575, Dec. 15, 2004.

McGregor et al., "Cardiac xenotransplantation: recent preclinical progress with 3-month median survival," J Thorac Cardiovasc Surg., 130(3):844-851, Sep. 2005.

(56) References Cited

OTHER PUBLICATIONS

McGregor et al., "Human CD55 expression blocks hyperacute rejection and restricts complement activation in Gal knockout cardiac xenografts," Transplantation, 93(7):686-692, Apr. 15, 2012.

Mohiuddin et al., "Current status of pig heart xenotransplantation," Int J Surg., 23(Pt B):234-239, Epub Aug. 28, 2015.

Ricci et al., "The utility of right ventricular endomyocardial biopsy for the diagnosis of xenograft rejection after CD46 pig-to-baboon cardiac transplantation," J Heart Lung Transplant., 26(10):1025-1032, Oct. 2007.

Schirmer et al., "Effective antiplatelet therapy does not prolong transgenic pig to baboon cardiac xenograft survival," Xenotransplantation, 11(5):436-443, Sep. 2004.

Tazelaar et al., "Comparison of Gal and non-Gal-mediated cardiac xenograft rejection," Transplantation, 91(9):968-975, May 15, 2011.

Teotia et al., "Prevention, detection, and management of early bacterial and fungal infections in a preclinical cardiac xenotransplantation model that achieves prolonged survival," Xenotransplantation, 12(2):127-133, Mar. 2005.

Warnecke et al., "Endothelial function in pigs transgenic for human complement regulating factor," Transplantation, 73(7):1060-1067, Apr. 15, 2002.

Weaver et al., "Rejection severity directly correlates with myocyte apoptosis in pig-to-baboon cardiac xenotransplantation," J Heart Lung Transplant., 24(7):841-847, Jul. 2005.

Xu et al., "Development and characterization of anti-Gal B cell receptor transgenic Gal-/- mice," Transplantation, 73(10):1549-1557, May 27, 2002.

Xu et al., "Serologic analysis of anti-porcine endogenous retroviruses immune responses in humans after ex vivo transgenic pig liver perfusion," ASAIO J., 49(4):407-416, Jul.-Aug. 2003.

Xu et al., "The in vitro and in vivo effects of anti-galactose antibodies on endothelial cell activation and xenograft rejection," J Immunol., 170(3):1531-1539, Feb. 1, 2003.

Yin et al., "CTLA-41g in combination with anti-CD40L prolongs xenograft survival and inhibits anti-gal ab production in GT-Ko mice," Am J Transplant., 2(1):41-47, Jan. 2002.

Yin et al., "Cutting Edge: NK cells mediate IgG1-dependent hyperacute rejection of xenografts," J Immunol., 172(12):7235-7238, Jun. 15, 2004.

\* cited by examiner

Figure 3

| Species | Gene Name | Gene Symbol | NCBI Ref. Seq. | Gene ID |
|---|---|---|---|---|
| Sus scrofa | Tetraspanin 29 | CD9 | NM_214006.1 | 397067 |
| Sus scrofa | Membrane cofactor protein | CD46 | NM_213888.1 | 396922 |
| Sus scrofa | Protectin | CD59 | NM_214170.1 | 397347 |
| *Bos taurus | Endothelial cell protein C receptor | PROCR | NM_174437.1 | 282005 |
| Sus scrofa | Annexin A2 | ANXA2 | NM_001005726.1 | 406192 |
| *Bos taurus | beta 1,4 N-acetyl-galactosaminyl transferase 2 | B4GALNT2 | XM_584835.3 | 508108 |

* The sequence with closest homology is presented. Porcine cDNA for this gene was not found through the BLAST search or porcine sequences detected were anonymous expressed sequence tag sequences without gene identification.

Figure 6

```
Pig     MTS----YSPRCLSILKILMVLLVLSVGLFMFQSVFLDTDFSLLNSPIPSFTLDAQTLKL  56
Human   MTS----GCSRFLWLLKILVIILVLGIVGFMFGSMFLQAVFSSPXPELPSPAPCVQKLKL  56
Mouse   MTSSVSFASFRFPWLLKIFVLMVGLATVAFMVRKVSLTIDFSIFXPKFPEFARVDEVLKL  60
        ***       *   **   ...   *   **   .   *   **      *  *   ***

Pig     LPEK--PDFYGENG--LFSKNQCQCDAFGHQESYNLEDAYDPQDLPAVNLRPQAELEHFQ  112
Human   LPEERLRNLFSYDGIWLFPKNQCKCEANKEQGGYNFQDAYGQSDLPAVKARRQAEFEHFQ  116
Mouse   LPEEHLRKLFTYSDIWLFPKNQCDCNSGKLRMKYKFQDAYNQKDLPAVNARRQAEFEHFQ  120
        ***         .   ** ****  *      .    *    ***   ***** ****  ****

Pig     RREGLPRPPPLLAQPNLPFCYPVHGVEVMPLHTIPIPGLRFEGPDAPIYEVTLTASLGTL  172
Human   RREGLPRPLPLLVQPNLPFCYPVHGVEVMPLHTVPIPSLQFEGPDAPVYEVTLTASLGTL  176
Mouse   RREGLPRPPPLLAPPNLPFCYPVHGVEVMPLHTILIPGLQYEGPDAPVYEVILXASLGTL  180
        ********  *** ********************.****.*****  *** ******

Pig     NALADVPDNVVRGRGQKQLNILTSSRELLNFILQHVTYTSTEYHLHRVDVVSLESKSSVA  232
Human   NTLADVPDSVVQGRGQKQLIISTSDRXLXFILQHVTYISTGYQHQKVDIVSLESRSSVA  236
Mouse   NTLADVPDDEVQGRGQRQLTISTRHRXVLNFILQHVTYTSTEYYLHKVDTVSMEYESSVA  240
        * ******  * *** ** .* ***  *  * ************ *   ** **  ****

Pig     KFPVTIRYPVMPKLYDPGPERKLRDLVTIATKTFLRPHKLMTMLRSVREYYPDLTVIVAD  292
Human   KFPVTIRHPVIPKLYDPGPERKLRNLVTIATKTFLRPHKLMLMLRSIREYYPDLTVIVAD  296
Mouse   KFPVTIKQQTVPKLYDPGPERKLRNLVTIATKTFLRPHKLKLLQSIKYYPDITVIVAD  300
        ******    .********* ** ***********.**** .*.* *** ******

Pig     DSREPLKITDSHVEYYTMPFCKGWFAGRNLAI*SQVTTKYVLWVDDDF*IPNSKTRIEALAD  352
Human   DSQKPLEIKDNHVEYYTMPFGKGWFAGRNLAI*SQVTTKYVLWVDDDFL*FNEETKIEVLVD  356
Mouse   DSREPLEINDDYVEYYTMPFCKGWFAGRNLAI*SQVTTKYVLWVDDDFL*FSDKTKIEVLVD  360
        ** ** *  ********  ***************************** *  ** ** *

Pig     VLEKTELDVVGGSVIENTFQFKLLLEQGKNGDCLHQQPGFFRPVDGFFDCVVTSGVVSFF  412
Human   VLEKTELDVVGGSVLGNVFQFKLLLEQSENGACLHKRMGFFQPLDGFFSCVVTSGVVNFF  416
Mouse   VLEKTELDVVGGSVQGNTYQFRLLYEQIKNGSCLHQRWGSFQALDGFPGCTLTSGVVNFF  420
        **************   *  **  **  ** * ** **  ** **** .* ******.**

Pig     LAHTERLQRIGFDPRLQRVAHSEFFIDGLGSLLVGSCPHVIIGHQPHLPVMDPELATLEG  472
Human   LAHTERLQRVGFDPRLQRVAHSEFFIDGLGILLVGSCPEVIIGHQSRSPVVDSELAALEX  476
Mouse   LAHTEQLRRVGFDPILQRVAHGEFFIDGLGRLLVGSCPGVIINHQVRTPPXDPXLAALEX  480
        ***** *   ***  *****  *******  ******  ** ***    *   *** **

Pig     NYTSYRANTEAQIKFKLALHYFKNYLQCATN      503
Human   TYNTYRSNTLTRVQFKLALHYFKNHLQCAANRC    509
Mouse   TYDKYRANTNSVIQFKVALQYFKNHLYCSTN      511
        .*  **.**    . .**.** ******  *  *..*
```

Figure 8

```
  M   T   S   Y   S   P   R   C   L   S   I   L   K   I   L
ATG ACT TCG TAC AGC CCT AGA TGT CTG TCG ATC CTC AAG ATA TTG   45

M   V   L   L   V   L   S   V   G   L   F   M   F   Q   S
ATG GTG CTT TTG GTC CTG AGC GTT GGA CTC TTT ATG TTC CAA AGC   90

V   F   L   D   T   D   F   S   L   L   N   S   P   I   P
GTG TTC CTC GAT ACA GAC TTC AGT CTC CTC AAC TCA CCC ATC CCG  135

S   P   T   L   D   A   Q   T   L   K   L   L   P   E   K
TCC CCC ACC CTG GAT GCG CAG ACG CTA AAG CTT CTA CCT GAG AAA  180

P   D   F   Y   G   E   N   G   L   F   S   K   N   Q   C
CCC GAT TTC TAC GGT GAA AAC GGG CTG TTC TCG AAA AAC CAG TGC  225

Q   C   D   A   F   G   H   Q   E   S   Y   N   L   E   D
CAA TGT GAC GCC TTC GGG CAT CAG GAA AGC TAT AAC TTG GAG GAT  270

A   Y   D   P   Q   D   L   P   A   V   N   L   R   R   Q
GCC TAC GAC CCG CAA GAC CTC CCC GCA GTG AAC CTG AGG AGA CAG  315

A   E   L   E   H   F   Q   R   R   E   G   L   P   R   P
GCT GAG CTC GAA CAC TTT CAG AGG AGA GAA GGG CTC CCT CGC CCA  360

P   P   L   L   A   Q   P   N   L   P   F   G   Y   P   V
CCG CCC CTG CTG GCT CAG CCC AAC CTC CCC TTT GGG TAC CCG GTC  405

H   G   V   E   V   M   P   L   H   T   I   P   I   P   G
CAC GGG GTG GAA GTG ATG CCT CTA CAC ACC ATC CCC ATC CCA GGC  450

L   R   F   E   G   P   D   A   P   I   Y   E   V   T   L
CTC CGG TTT GAA GGA CCT GAT GCT CCC ATC TAT GAG GTC ACC CTG  495

T   A   S   L   G   T   L   N   A   L   A   D   V   P   D
ACA GCT TCT CTG GGG ACA CTG AAC GCC CTT GCT GAC GTC CCA GAC  540

N   V   V   R   G   R   G   Q   K   Q   L   N   I   L   T
AAT GTG GTG AGG GGC AGA GGC CAG AAG CAG CTG AAC ATT TTG ACC  585

S   S   R   E   L   L   N   F   I   L   Q   H   V   T   Y
AGT AGC CGG GAG CTT TTG AAT TTC ATC CTC CAG CAT GTG ACA TAC  630

T   S   T   E   Y   H   L   H   R   V   D   V   V   S   L
ACG AGC ACA GAG TAC CAC CTC CAC AGA GTG GAT GTG GTG AGT CTG  675

E   S   K   S   S   V   A   K   F   P   V   T   I   R   Y
GAG TCC AAG TCC TCA GTG GCC AAG TTT CCA GTG ACC ATC CGC TAT  720
```

Figure 8 (continued)

```
     P   V   M   P   K   L   Y   D   P   G   P   E   R   K   L
    CCT GTC ATG CCC AAG TTA TAT GAC CCT GGA CCA GAG AGG AAG CTC    765

R   D   L   V   T   I   A   T   K   T   F   L   R   P   H
    CGA GAC CTG GTG ACC ATT GCC ACC AAA ACC TTC CTC CGT CCC CAC    810

K   L   M   T   M   L   R   S   V   R   E   Y   Y   P   D
    AAG CTC ATG ACC ATG CTC CGG AGT GTT CGT GAG TAC TAC CCA GAC    855

L   T   V   I   V   A   D   D   S   K   E   P   L   K   I
    CTG ACG GTG ATC GTG GCC GAT GAC AGC AAG GAG CCC CTG AAA ATC    900

T   D   S   H   V   E   Y   Y   T   M   P   F   G   K   G
    ACT GAC AGC CAC GTG GAG TAT TAC ACC ATG CCA TTT GGG AAG GGC    945

W   F   A   G   R   N   L   A   I   S   Q   V   T   T   K
    TGG TTT GCT GGC AGG AAC CTG GCC ATA TCT CAG GTC ACC ACC AAA    990

Y   V   L   W   V   D   D   D   F   I   F   N   S   K   T
    TAT GTG CTC TGG GTG GAC GAT GAC TTC ATC TTC AAC AGC AAG ACC    1035

R   I   E   A   L   A   D   V   L   E   K   T   E   L   D
    AGG ATC GAG GCG CTG GCG GAC GTC CTA GAG AAA ACG GAA CTG GAC    1080

V   V   G   G   S   V   I   E   N   T   F   Q   F   K   L
    GTG GTA GGT GGC AGC GTG ATT GAA AAC ACA TTC CAG TTC AAG CTG    1125

L   L   E   Q   G   K   N   G   D   C   L   H   Q   Q   P
    TTG CTG GAG CAG GGG AAG AAT GGC GAC TGT CTC CAC CAG CAG CCA    1170

G   F   F   R   P   V   D   G   F   P   D   C   V   V   T
    GGA TTT TTC CGG CCC GTG GAT GGC TTC CCC GAC TGC GTG GTG ACC    1215

S   G   V   V   S   F   F   L   A   H   T   E   R   L   Q
    AGT GGT GTT GTC AGC TTC TTC CTG GCT CAC ACA GAG CGA CTC CAA    1260

R   I   G   F   D   P   R   L   Q   R   V   A   H   S   E
    AGA ATT GGC TTC GAC CCC CGG CTG CAG CGA GTG GCT CAC TCA GAG    1305

F   F   I   D   G   L   G   S   L   L   V   G   S   C   P
    TTC TTT ATT GAT GGG CTC GGG AGC CTG CTC GTG GGG TCC TGC CCA    1350

H   V   I   I   G   H   Q   P   H   L   P   V   M   D   P
    CAC GTG ATC ATA GGT CAC CAG CCC CAT TTA CCA GTG ATG GAC CCA    1395

E   L   A   T   L   E   G   N   Y   T   S   Y   R   A   N
    GAG CTG GCC ACC CTG GAG GGG AAC TAC ACC AGT TAT CGG GCC AAC    1440

T   E   A   Q   I   K   F   K   L   A   L   H   Y   F   K
    ACC GAA GCC CAG ATC AAA TTC AAG TTG GCT CTC CAC TAC TTC AAG    1485

N   Y   L   Q   C   A   T
    AAC TAT CTC CAA TGT GCC ACC TAA                               1509
```

Figure 9

```
Intron-8
GAC AGC CAC GTG GAG TAT TAC GCC ATG CCA TTT GGG AAG gtatattcct      49
cccagagggg gagacacggg caccctggga ccagagggcc ccagggtcaa gtggtaccct  109
ggttgggggct gcttcggggt tggggggggac cctctcacgg cagcaggatc cttgggggc  169
ggaggggtggg gactcctctg agtccccctgg ctgcctccaa attcccggag aaatcaggtc  229
actctccctt tcctgcagtg acggggtggg taatccgtct ttcctcacgc ttggtgtgga  289
aattgatgga ggtccttgta agcgactggc ggtgtctgac gctctaaggt ttcctgatac  349
gcaggtccca cagcagagaa acctctctca tgatttcacc cttgctgggg cgtctctctc  409
cgcgcccccac accttccctc gagcacaccg ggaggaagtg gatgttaccc cttccagaga  469
gccccacccct ccagcatctt ccaggcaaca cagggcgaaa gggccacaaa gactgtcagg  529
tgtaaaggga cttgcatcca tccctcaagc cacacggcca aggaaggact ttctcgtctc  589
cagagagtcc ctctccttct tccagggtct ctgagacatg gactccttt agcccagagg  649
ttttcagcca ctgtctgggg ggcagcctga cccttgggag ctgagaaagc cccaggtga  709
tgctaggagg cagcggggcg ggcaaccacg gtctaacct cctgccctc gcag          762
GGC TGG TTT GCT GGC AGA AAC CTG GCC ATA TCT CA                     797
```

Figure 10A

```
Intron-10
G CGA CTC CAA AGA ATT GGC TTC GAC CCC CGG CTG CAG CGA GTG GCT CAC         49
TCA cgtgggagg ctggaaggc aagaagcgag ctggctgtg cgctggcttc agaagtctct       111
ttctgaggga gggcggggcc ccactgctca gggaagcggc cccttctccc caaactaggg       171
agctcttggt ctctcttgcc tccctccacc ttcgtgtctc ccataggcta ttcctgcttc       231
tccgagacac ccttctacct cctctccctg cagctctgcc ccttccctct ttccttgtct       291
tgctgctgct cctccttttt tttgccttg tagggctgca cccatggcat gtggaggttc        351
ccaggctagg ggttgaattg gagcttttgc tcccggccta tgccagagcc acagcaacac       411
gggatctgag ctgcttctgt gacctacacc acagctcagg gcagcgccag atccttaacc       471
cactgaacga ggccagggac cgaaccacca acctcatggt tcctagtcgg attcattaac       531
cactacgcca tgaccggaat ttcctgctcc tcctttccca gacatccttc totgtttagc       591
tgcagctggt gagcagcacc ccaactcttc ccctctcatt cctcccagtc ctgggtcta        651
ctaatctgtg tctctctgct gatatctgct tgatcttcca actcagtggc tttgccatgg       711
gactgaacct cccagaaata gaagctatt ccccccgccc cagcccctcc cccagagtcg        771
cagtattggc ccgggtctct ggtttgaagc tcacgtttcc ttctcgcgct ctctccctct       831
cttggca GAG TTC TTT ATT GAT GGG CTC CTC GGG AGC CTG CTC GTG GGG TCC TGC 883
CCA CAC GTG ATC ATA GGT CAC CA                                          906
```

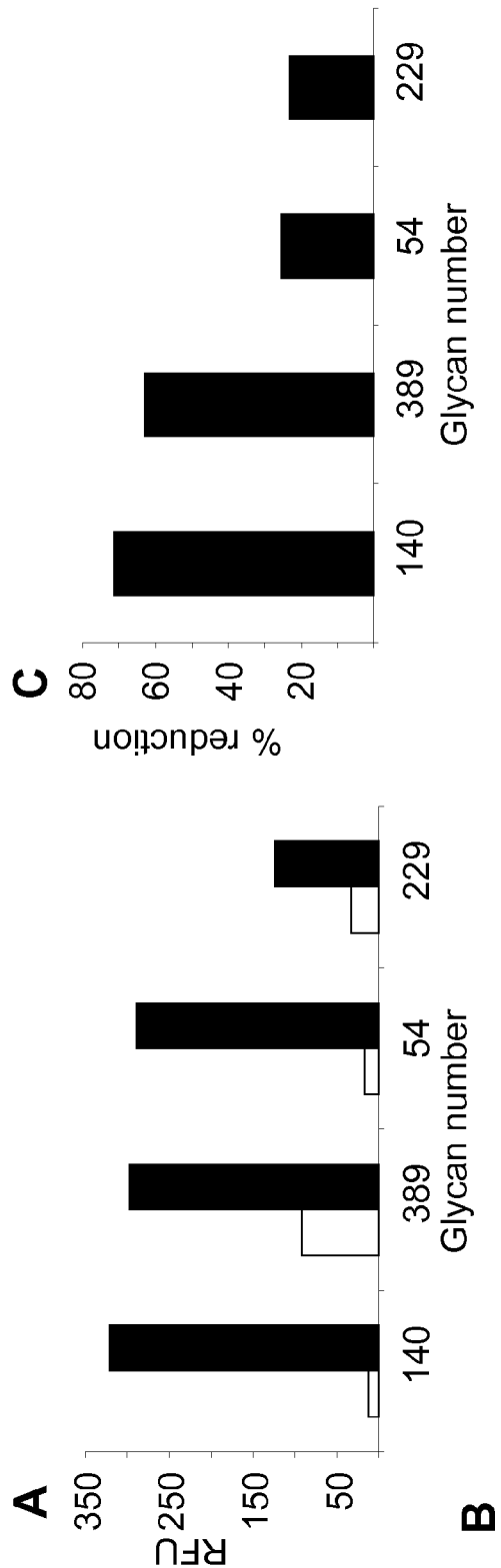

IMPLANTATION OF A CARDIAC XENOGRAFT FROM A B4GALNT2KO AND GTKO TRANSGENIC PIG TO REDUCE IMMUNOGENICITY

CROSS-REFERENCE TO RELATED APPLICATIONS

This application is a National Stage application under 35 U.S.C. 371 of International Application No. PCT/US2011/031976, having an International Filing Date of Apr. 11, 2011, which claims the benefit of priority to U.S. Provisional Application Ser. No. 61/332,127, filed May 6, 2010. The disclosure of the prior application is considered part of (and is incorporated by reference in) the disclosure of this application.

STATEMENT AS TO FEDERALLY SPONSORED RESEARCH

This invention was made with government support under AI066310 awarded by the National Institutes of Health. The government has certain rights in the invention.

BACKGROUND

1. Technical Field

This document relates to methods and materials involved in reducing cardiac xenograft rejection. For example, this document provides methods and materials for preparing transgenic pigs expressing reduced or no endogenous $Sd^a$, reduced or no endogenous SDa-like glycans derived from the porcine β1,4 N-acetyl-galactosaminyl transferase 2 (B4GALNT2) glycosyltransferase, and/or reduced or no endogenous α-Gal antigens, methods and materials for modifying a xenograft recipient's immunological response to non-Gal antigens (e.g. CD46, CD59, CD9, porcine endothelial cell protein C receptor (PROCR) and annexin A2 (ANXA2)) to reduce cardiac xenograft rejection, and methods and materials for monitoring the progression, if any, of xenotransplant immunologic rejection.

2. Background Information

There is a chronic shortage of organs for transplantation. This is particularly the case in cardiac transplantation where approximately 2300 heart transplants are performed annually but up to 50,000 patients in chronic heart failure could benefit from a transplant. Xenotransplantation (transplantation from one species to another) could provide an unlimited supply of organs if successful. Xenotransplantation can be limited by an immunological rejection of the transplanted organ. Initially this rejection can be due to preformed antibodies present in humans and Old World primates that bind to a carbohydrate modification called the α-Gal antigen. This antigen can be produced in great abundance in pigs and other mammalian species. The combination of abundant α-Gal antigen in pig organs and high levels of preformed anti-Gal antibody in nonhuman primates (a model for humans) can result in a devastating hyperacute rejection of the graft usually within hours.

SUMMARY

This document provides methods and materials for reducing cardiac xenograft rejection. For example, this document provides methods and materials for preparing transgenic pigs expressing reduced or no endogenous $Sd^a$ or SDa-like glycans produced from a porcine β1,4 N-acetyl-galactosaminyl transferase 2 (B4GALNT2) glycosyltransferase and reduced or no endogenous α-Gal antigens produced from the porcine α1-3 galactosyl transferase (GT) glycosyltransferase, methods and materials for modifying a xenograft recipient's immunological response to non-Gal antigens (e.g., CD46, CD59, CD9, PROCR and ANXA2) to reduce cardiac xenograft rejection, and methods and materials for monitoring the progression of, if any, xenotransplant immunologic rejection. In some cases, this document provides methods for implanting a pig xenograft heart into a human. The pig xenograft donor can be a pig that contains genetic disruptions in α1-3 galactosyl transferase (GT) nucleic acid and β1,4 N-acetyl-galactosaminyl transferase 2 (B4GALNT2) nucleic acid. Such pigs can lack the ability to express $Sd^a$ or SDa-like glycans and α-Gal antigens. The methods and materials described herein can be used to reduce immunogenicity of the pig to primate cardiac xenograft upon implantation and prolong the durability of the xenograft. This can benefit patients in chronic heart failure on the heart transplant waiting list for a donor heart.

In general, one aspect of this document features a method of providing a primate with a cardiac xenograft. The method includes implanting the cardiac xenograft into the primate, wherein the xenograft has decreased or no expression of α-Gal antigen and decreased or no expression of $Sd^a$ or SDa-like antigen on the endothelial cell membranes.

In another embodiment, this document features a method of providing decreasing immune rejection of a cardiac xenograft. The method includes inducing antigen specific tolerance in a primate recipient wherein the antigen is at least one polypeptide selected from the group consisting of CD46, CD59, CD9, porcine PROCR and ANXA2.

In another embodiment, this document features a method for measuring the progress of cardiac xenograft immune rejection. The method includes monitoring a primate recipient antibody response to an individual non-Gal endothelial cell membrane antigen present on the xenograft, wherein the non-Gal endothelial cell membrane antigen is selected from the group consisting of CD46, CD59, CD9, porcine PROCR and ANXA2.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 3 is a table listing the results of BLAST searches of the NCBI GenBank database with the cDNA insert nucleic acid sequence for each of the six individual clones identified in the library screening.

FIG. 6. Alignment of pig (SEQ ID NO:1), human (SEQ ID NO:2), and mouse (SEQ ID NO:3) B4GALNT2 amino acid sequences. A * indicates amino acid identity. Conservation is highest in the C-terminal region. Shaded regions highlight the conservation of the relationship between the exon boundaries of the genomic DNA, which are shaded dark and light, in the amino acid sequences of the protein for human and mouse. Boldfaced italic amino acids (325-339) indicated in the region encoded by exon 9 correspond to a conserved sequence detected in all three species of B4GALNT2 and detected in the human GM2 synthase. This sequence includes an acidic "DXD" motif conserved in 13 glycosyltransferase families of the CAZy classification. The DXD motif is required for GM2 enzymatic activity.

FIG. 8. The porcine cDNA (SEQ ID NO:4) and amino acid (SEQ ID NO:1) sequences. Vertical lines indicate the putative locations of exon boundaries based on the human and murine B4GALNT2 genes. The conserved amino acid sequence associated with the catalytic site of the enzyme is underlined. Boldface nucleotides indicate the position of PCR primers used to amplify intervening intron sequences from genomic porcine DNA. Arrows indicate the orientation of the primer for PCR.

FIG. 9. Genomic porcine nucleotide sequence (SEQ ID NO:5) for putative intron 8. Porcine genomic DNA sequences were amplified using primers from the B4GALNT2 cDNA corresponding to exons 8 and 9 in the conserved human and murine B4GALNT2 genes. Coding sequences from the porcine B4GALNT2 cDNA are presented in upper case and underlined. Boldface nucleotides indicate the positions of PCR primers used for amplification. Lowercase nucleotides represent intron sequence.

FIG. 10A. Genomic porcine nucleotide sequence (SEQ ID NO:6) for putative intron 10. Porcine genomic DNA sequences were amplified using primers from the B4GALNT2 cDNA corresponding to exons 10 and 11 in the conserved human and murine B4GALNT2 genes. Coding sequences from the porcine B4GALNT2 cDNA are presented in upper case and underlined. Boldface nucleotides indicate the positions of PCR primers used for amplification. Lowercase nucleotides represent intron sequence.

FIG. 15. Identification of potential non-Gal antibody oligosaccharide targets present on HEK-B4GALNT2 cells. A. Comparison of pretransplant (open) and necropsy (filled) IgG reactivity to four glycans present on the Mammalian printed glycan array (Version 4.2). Increased reactivity to these glycans is evident in necropsy serum. B. Structure of the oligosaccharides. Numbers correspond to values in the graphs. C. Shows the percent reduction in IgG binding after absorption of necropsy serum with HEK-B4GALNT2 cells. Abbreviations: Gal; galactose, GalNAc; N-Acetylgalactosamine, Glc; glucose, Neu5Ac; N-Acetylneuraminic acid, Man; mannose, GlcNAc; N-Acetylglucosamine

DETAILED DESCRIPTION

Figure 1:
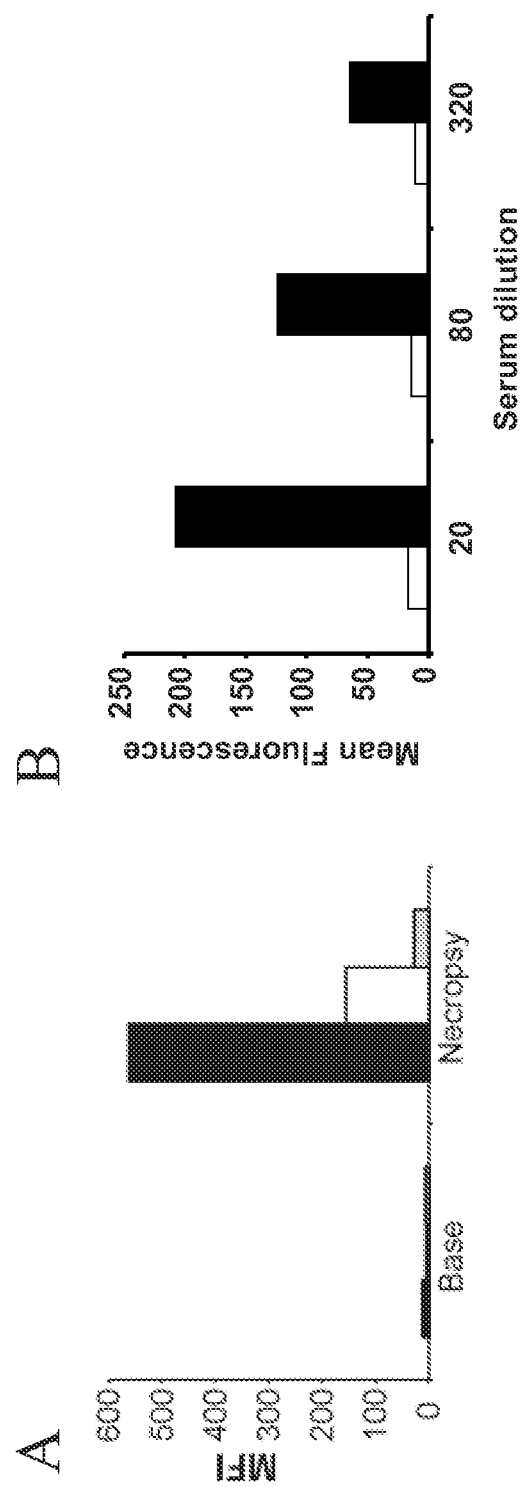
FIG. 1. Bar graphs depicting the non-Gal antibody levels in sensitized baboon serum used to identify non-Gal antigens. Non-Gal antibody responses were determined using flow cytometry to measure the extent of IgG binding to α-Gal antigen knock-out (GTKO) porcine aortic endothelial cells (PAECs). A. Reproduction of FIG. 1D from Davila et al. *Xenotransplantation*, 13(1):31-40 (2006) comparing baseline (Base) and necropsy IgG binding of three GT-positive cardiac xenograft recipients. B. Comparison of pretransplant (white bars) and necropsy (black bars) IgG binding to GTKO PAECs from a GTKO graft recipient. All recipients show an increase in anti-pig non-Gal IgG after transplant.

This document provides methods and materials for reducing cardiac xenograft rejection. Provided herein are methods and materials for identifying pig heart non-Gal endothelial cell membrane antigens. Also provided are methods and materials for making transgenic pigs having disruptions in the endogenous β1,4 N-acetyl-galactosaminyl transferase 2 (B4GALNT2) nucleic acid sequence. Such transgenic pigs can be breed with transgenic pigs having disruptions in the endogenous GT nucleic acid sequence in order to produce transgenic pigs having disruptions in both nucleic acid sequences. Also provided are methods and materials for inducing immunological tolerance in a primate to pig heart endothelial cell membrane antigens (e.g. CD46, CD59, CD9 and porcine PROCR) prior to xenograft implantation and methods and materials for monitoring cardiac xenograft rejection.

Identifying Pig Heart Non-Gal Endothelial Cell Membrane Antigens

This document provides methods and materials to identify non-Gal antigen targets of pig-to-primate cardiac xenograft immune rejection. As used herein, "non-Gal" refers to antigens different from the galactose α1,3 galactose β1,4N-acetylglucosamine trisaccharide (Gal α1-3Galβ1-4GlcNac; i.e., the α-Gal antigen).

An antibody response to the endothelium of the xenograft is widely considered to be the primary point of the immune response which initiates delayed xenograft rejection. Xenograft rejection is believed to occur due to chronic activation of the vascular endothelium of the graft by antibody binding or injury to the vascular endothelium through antibody directed cell cytotoxicity or complement mediated damage. These processes would promote the formation of a thrombogenic vasculature, resulting in microvascular thrombosis that, if unchecked, would lead to ischemic injury, culminating in coagulative necrosis of the myocardium. Prior to the development of GTKO pigs, rejection was thought to be induced primarily through the effects of anti-Gal antibody. The development of pigs deficient in the expression of the α-Gal antigen eliminated a role for anti-Gal antibody and revealed the significance of non-Gal antibody responses (Byrne et al., *Xenotransplantation*, 15:268-276 (2008)).

Any suitable method can be used to detect cardiac antigens that bind to antibodies from primate recipients of pig GT-positive and pig GTKO donor hearts. Examples include, but are not limited to, mammalian cDNA expression libraries screened with sensitized serum and sorted by flow cytometry, two-dimensional Western blot analysis, high throughput screening and proteomic analysis. Methods to identify such detected polypeptides include, but are not limited to mass spectrometry, nucleotide sequencing, amino acid sequencing and high performance liquid chromatography.

Preparing β1,4 N-acetyl-galactosaminyl Transferase 2 and α1-3 galactosyl Transferase Knock-Out Pigs This document provides transgenic pigs whose genomes have disruptions in the endogenous B4GALNT2 and GT nucleotide sequences. The human and mouse B4GALNT2 enzyme catalyzes the addition of N-acetylgalactosamine to terminal α2,3-sialylated galactose residues in the β1,4 linkage to produce the $Sd^a$ antigen. This enzymatic activity has been detected in several species including the pig. The porcine B4GALNT2 gene identified herein is homologous to the human and murine genes and is expected to have similar enzymatic activity. The GT enzyme catalyzes the synthesis of galactose α1,3 galactose β1,4N-acetylglucosamine trisaccharide (the α-Gal antigen). The α-Gal antigen is found in most mammals, including pigs, but not in Old World monkeys, apes or humans.

Transgenic pigs whose genomes have disruptions in the endogenous porcine B4GALNT2 and GT nucleotide sequences can have reduced or no detectable porcine B4GALNT2 activity and reduced or no detectable GT activity. Cells from such transgenic pigs can have reduced or no detectable expression of the Sd$^a$ or SDa-like glycans and α-Gal antigens on their surfaces. Such reduced or undetectable Sd$^a$ or SDa-like glycans and α-Gal glycan expression is relative to control, non-transgenic pigs. For example, transgenic pigs having disruptions in the endogenous porcine B4GALNT2 and GT nucleotide sequences can present at least 50 percent less Sd$^a$ and α-Gal antigen (e.g. less than 40 percent, less than 25 percent, less than 10 percent or less than 3 percent expression) as compared to control, non-transgenic pigs.

The term "endogenous" as used herein in reference to nucleic acid sequences and an organism refers to any nucleic acid sequence that is naturally present in the genome of that organism. An endogenous nucleic acid sequence can comprise one or more gene sequences, intergenic sequences, portions of gene sequences or intergenic sequences, or combinations thereof. The terms "B4GALNT2 nucleic acid sequence" and "GT nucleic acid sequence" as used herein, refer to the entire procine B4GALNT2 and GT gene sequences, including introns, exons, and regulatory regions.

Any suitable method can be used to generate pigs whose genomes contain disruptions in the endogenous B4GALNT2 and GT nucleic acid sequences. For example, transgenic porcine cells can be used for nuclear transplantation. Transgenic cells can be produced by introducing a knock-out construct into wild-type porcine cells. As used herein, a "knock-out construct" refers to a nucleic acid construct that is designed to disrupt an endogenous nucleic acid sequence (i.e., an endogenous porcine B4GALNT2 nucleic acid sequence or an endogenous GT nucleic acid sequence). Transgenic pigs whose genomes contain a disruption only in the GT nucleic acid sequence can be obtained commercially or can be produced as described elsewhere (see, e.g., Nottle et al., *Xenotransplantation*, 14(4): 339-344 (2007). The methods and materials provided herein can be used to design a disruption in a porcine endogenous B4GALNT2 nucleic acid sequence. A disruption can be positioned at many sites in the endogenous porcine B4GALNT2 nucleic acid sequence. Examples of disruptions include, but are not limited to, deletions in the native gene sequence and insertions of heterologous nucleic acid sequences into the native gene sequence. Examples of insertions can include, but are not limited to, artificial splice acceptors coupled to stop codons or splice donors coupled to fusion partners such as GFP. A knock-out construct can contain sequences that are homologous to the endogenous B4GALNT2 nucleic acid sequence or to sequences that are adjacent to the endogenous B4GALNT2 nucleic acid sequence. In some cases, a knock-out construct can contain a nucleic acid sequence encoding a selection marker (e.g., antibiotic resistance, a fluorescent reporter (e.g., GFP or YFP), or an enzyme (e.g., β-galactosidase)) operatively linked to a regulatory sequence (e.g., a promoter). A knock-out construct can include other nucleic acid sequences such as recombination sequences (e.g., loxP sequences, see Sendai, et al., *Transplantation*, 81(5):760-766 (2006)), splice acceptor sequences, splice donor sequences, transcription start sequences, and transcription stop sequences. Disruptions in the endogenous B4GALNT2 nucleic acid sequence can result in reduced expression of the gene or non-functional truncations or fusions of the encoded polypeptide.

Transgenic cells having a disruption in the endogenous B4GALNT2 nucleic acid sequence can be either adult or fetal cells and can be from primary or established cell lines. For example, transgenic fetal porcine fibroblasts can be fused with enucleated oocytes. Fused, activated oocytes can be cultured to the blastocyst stage, and implanted into a recipient. See, Arat, et al., *Biol. Reprod.*, 66(6):1768-1774 (2002); and DeBoer, et al., U.S. Pat. No. 5,633,076. Adult somatic cells of any cell type including, for example, granulosa cells and fibroblast cells, also can be used to produce transgenic pigs (Arat, et al., *Mol. Reprod. Dev.*, 60(1):20-26 (2001); and Arat, et al., (2002), supra, respectively). Nuclei can be removed from genetically modified adult somatic cells, and transplanted into enucleated oocytes. After activation, the eggs can be cultured to the 2-8 cell stage, or to the blastocyst stage, and implanted into a suitable recipient (DeBoer, et al., supra). Transgenic pigs heterozygous for the disrupted B4GALNT2 gene can be mated to produce homozygous transgenic pigs.

Transgenic pigs can be identified using any appropriate method. For example, cells from animals obtained using nuclear transplantation can be assessed for endogenous B4GALNT2 nucleic acid sequence disruption, B4GALNT2 RNA expression, or B4GALNT2 polypeptide expression. For example, endogenous B4GALNT2 nucleic acid sequence disruption can be identified using methods including southern blotting and PCR. B4GALNT2 RNA expression can be determined using methods such as Northern blot analysis, RT-PCR and fluorescent in situ hybridization. B4GALNT2 polypeptide expression can be determined using methods such as western blot analysis, immunohistochemistry, immunofluorescence, and detecting expression of the Sd$^a$ antigen on tissue sections. The methods for identifying transgenic pigs listed are intended to provide examples and are not in any way meant to limit the scope of the invention.

To determine if the B4GALNT2 antigen is present on the surface of cells from heterozygous or homozygous transgenic animals, tissue can be removed from the animal and then embedded using, for example, OCT (TISSUE-TEK, Sakura) embedding medium. Tissues can be sectioned, placed on glass slides, air-dried, and stored at −80° C. until use. The sectioned tissues can be stained for the Sd$^a$ antigen after fixing the sections in acetone, washing in water, blocking the slides, then incubating with the *Dolichos biflorus* (DBA) lectin. DBA is commercially available (e.g., from United States Biological (Swampscott, Mass.)). DBA can be labeled. Suitable labels include, without limitation, radionuclides (e.g., 125I, 131I, 35S, 3H, 32P, 33P, or 14C), fluorescent moieties (e.g., fluorescein, PerCP, rhodamine, or phycoerythrin), luminescent moieties (e.g., QDot Nanoparticles from Quantum Dot Corporation, Palo Alto, Calif.), or enzymes (e.g., alkaline phosphatase or horseradish peroxidase). DBA can be directly or indirectly labeled. Methods of indirect labeling can include, for example, conjugating the DBA with biotin then contacting the DBA-biotin with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multilayer" assays) familiar to those in the art can be used to enhance the sensitivity of assays.

Transgenic pigs whose genomes have disruptions in both the endogenous B4GALNT2 and GT nucleotide sequences can be obtained by breeding. Crossing a pig that has little or no Sd$^a$ antigen expression due to a disruption in the B4GALNT2 nucleotide sequence with a pig that has little or no α-Gal antigen expression due to a disruption in the GT nucleotide sequence can be performed to produce transgenic pigs with disruptions in both B4GALNT2 and GT nucleotide sequences. It can be determined if the offspring of the mating contain disruptions in both the endogenous B4GALNT2 and GT nucleotide sequences by RT-PCR, Northern blot analysis, nucleotide sequencing, immunoblot analysis, PCR, Southern blot analysis, flow cytometry with DBA lectin and other methods known in the art.

Modifying the Xenograft Recipient's Immunological Response to Non-Gal Antigens

The term "tolerance" as used herein refers to the specific immunological unresponsiveness to an antigen resulting from a previous exposure to such antigen. Antigen specific tolerance can be induced in a mammal (for example, mouse, rat, rabbit, dog, pig, goat, cow, Old World primate, human, etc.) by any mechanism known in the art. For example, molecular chimerism can be used to induce antigen specific tolerance in a recipient nonhuman primate. A retroviral or lentiviral vector encoding non-Gal antigens can be used to transduce recipient bone marrow derived hematopoietic stem cells. Such cells can be reintroduced to the nonhuman primate recipient prior to xenotransplantation. These transduced cells will travel to the immune compartments, establish a level of molecular chimerism and express the non-Gal antigens in the context of "self" without generating inflammatory co-signals. This will modulate the immune response to these non-Gal antigens as they will now be perceived as "self."

As another example, antigen specific tolerance can also be induced by ex vivo exposure of immune cells from a nonhuman primate recipient to an alloantigen (e.g. non-Gal antigen). Dendritic cells (DCs) act to present foreign antigens to T lymphocytes. When this presentation occurs under inflammatory conditions where both the antigen and secondary co-stimulating signals are present, DCs induce T cell activation. In the absence of inflammation or co-stimulatory signals, DC presentation of antigen to T cell will induce a state of tolerance either through T cell deletion, anergy or the expansion of antigen specific T regulatory cells Immature DCs are isolated from the nonhuman primate recipient prior to transplantation and exposed to purified non-Gal antigens (e.g. CD46, CD59, CD9 and porcine PROCR), cells expressing the non-Gal antigens (e.g. HEK cells or any mammalian cell line that does not express α-Gal), or exosomes from apoptotic cells that express the non-Gal antigens. The antigen pulsed DCs are then returned to the recipient prior to transplantation. The effectiveness of the procedure prior to and after xenotransplantation can be monitored using standard T cell proliferation assays where recipient T cells are stimulated by non-Gal antigens or cells expressing the non-Gal antigens.

Measuring the Progress of Pig Heart Xenograft Rejection

The polypeptide non-Gal antigens (i.e. CD46, CD59, CD9 and porcine PROCR) can be expressed in any mammalian cell line that does not express α-Gal (i.e. human, ape and Old World primate cell lines). For example, the polypeptide non-Gal antigens can be expressed in Human Embryonic Kidney 293 cells (ATCC, (Manassas, Va.)). While mammalian cells were used to express recombinant polypeptide non-Gal antigens, bacteria, yeast or insect cells can be used to produce the recombinant non-Gal antigens. These recombinant polypeptides can include the entire amino acid sequence or can be limited to the extracellular domain or some other subset of the amino acid sequence involved in binding to the non-Gal antibody. In some cases, the polypeptide non-Gal antigen cDNAs can be expressed as fusion proteins. These may include, but are not limited to, various polypeptide tags (i.e. 6× histidine tags, Flag tags, in vivo biotinylation sequences, myc tags, the immunoglobin constant region and other commonly used sequences designed to assist purification of recombinant proteins). These polypeptide tags can be located at either the amino or carboxyl terminus of the recombinant non-Gal antigens.

The recombinant non-Gal antigens can be bound to solid substrates and used to establish assays for monitoring non-Gal antigen immune responses. For example, the recombinant proteins can be bound to ELISA plates or spotted onto paper or glass supports. These substrates can be used to assay the presence of non-Gal antibody using standard ELISA and protein array methods known in the art. Recombinant non-Gal antigen can also be attached to flow cytometry beads and antibody binding to these beads determined using fluorochrome conjugated anti-human IgG or IgM which cross reacts with nonhuman primate IgG or IgM. Peptide sequences from the non-Gal antigens that bind preformed or induced non-Gal antibody can also be used as substrate for monitoring non-Gal antigen immune responses.

The invention will be further described in the following examples, which do not limit the scope of the invention described in the claims.

EXAMPLES

Example 1

Identifying Non-Gal Antigens Present on the Endothelial Cell Membranes of Pig Hearts Involved in Immunologic Xenograft Rejection Heterotopic pig-to-primate cardiac xenografts were performed using GT-positive and GTKO donor hearts without immunosuppression. See Davila et al., *Xenotransplantation*, 13(1):31-40 (2006). Sera obtained at necropsy was screened by flow cytometry to measure IgG binding to GTKO porcine aortic endothelial cells (PAECs). Serum from both GT-positive and GTKO recipients showed an induced antibody response to non-Gal antigens as evidenced by increased IgG binding to GTKO PAECs in necropsy sera compared to pre-transplant sera (FIG. 1). This necropsy sera was used for the library screen.

Figure 2:
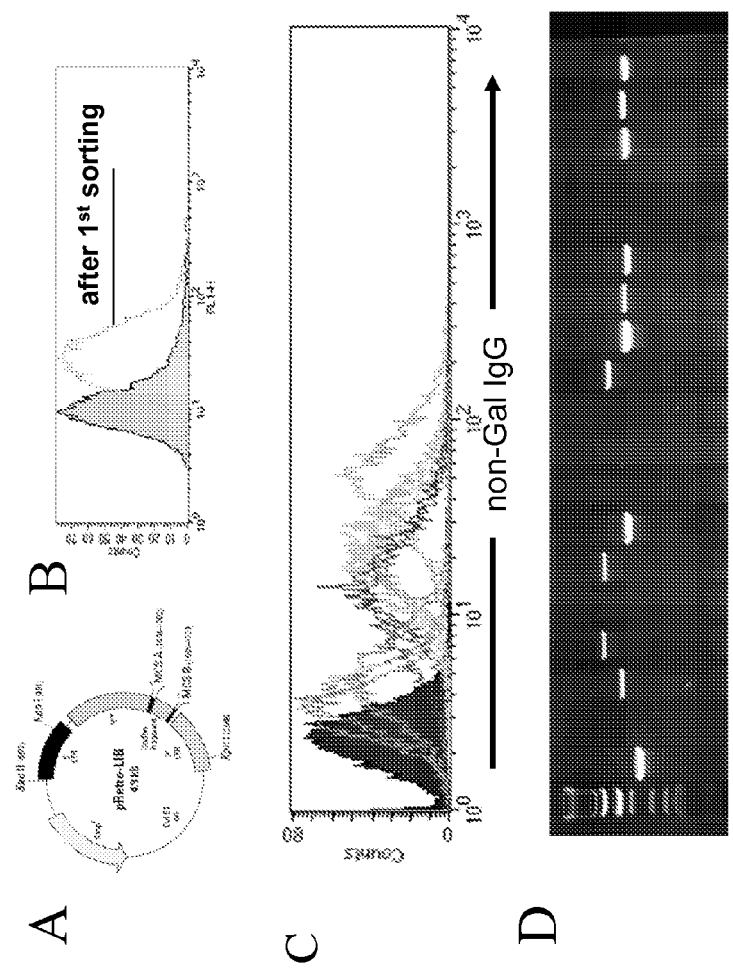
FIG. 2. Expression library screening and analysis. A. The map of the pRETRO-Lib vector used to clone the cDNA library from GT+ and GTKO porcine aortic endothelial cell mRNA. B. Human Embryonic Kidney 293 (HEK) cells infected with the pRETRO-PAEC viral library were stained with sensitized xenograft recipient sera. The brightest 10-30 percent of the cells were collected by cell sorting and regrown for additional rounds of enrichment. The filled distribution is antibody binding to the original infected population. The thin line is the population of selected cells restained with sensitized serum after 48 hours of growth. For each library screen, 3-7 rounds of enrichment were performed after which individual cells were sorted to 96-well plates, expanded and individually analyzed for IgG binding. C. Flow cytometry of individual pRETRO-PAEC library infected clones illustrating a variety of different levels of antibody binding. Filled histogram is a negative control that does not bind IgG. Thin lines represent IgG binding to individual clones. D. Library cDNA is recovered from genomic DNA of individual clones using PCR primers that flank the multiple cloning site (MCS) of the vector.
Figure 4:
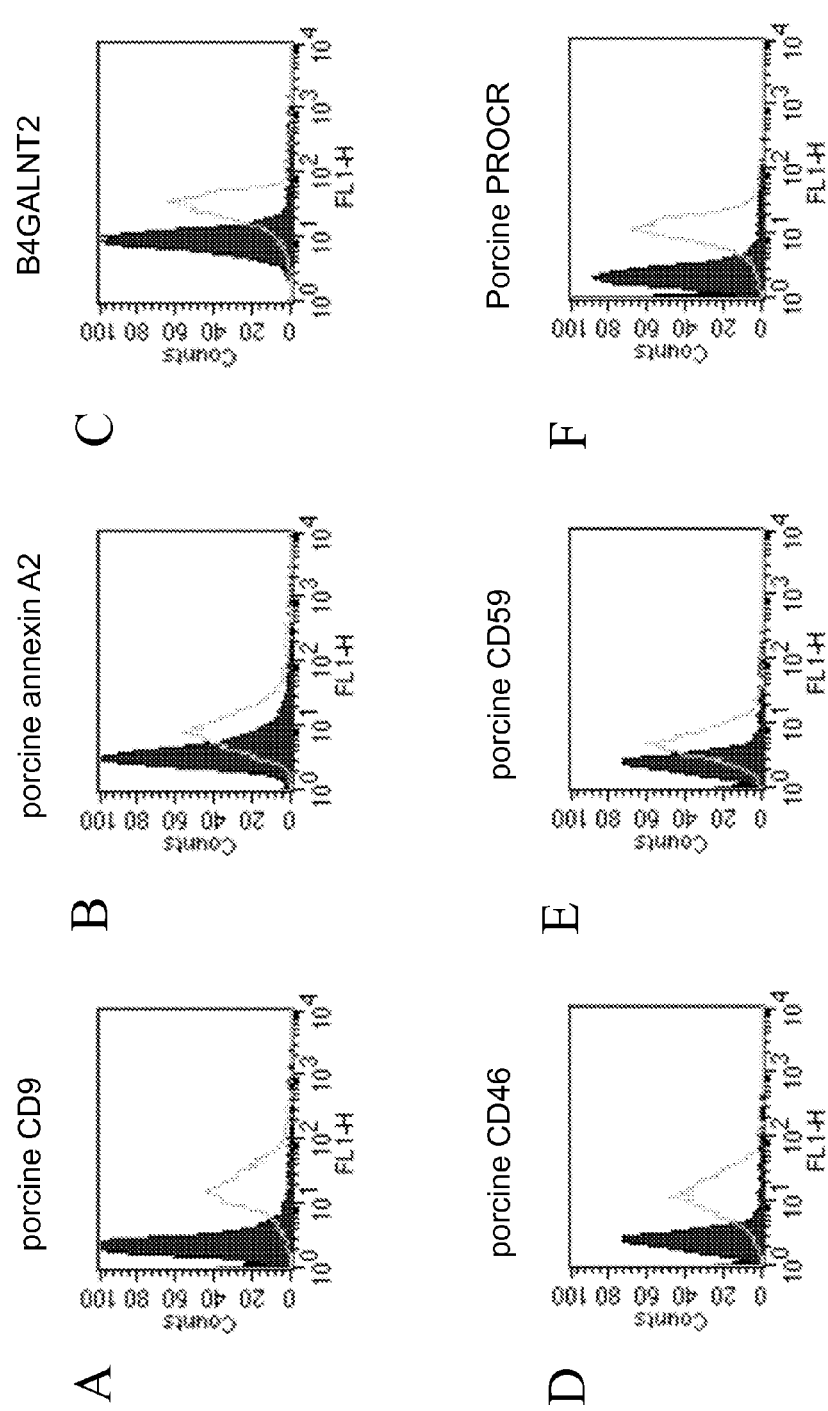
FIG. 4. Initial identification of pRETRO-PAEC infected HEK cells expressing non-Gal PAEC antigens. The thin line represents sensitized baboon serum binding to individual pRETRO-PAEC library infected HEK cells isolated by flow cytometry and cell sorting. The background (filled histogram) is sensitized baboon serum staining uninfected HEK cells or HEK cells infected with an unrelated retrovirus. Cell lines expressing A. porcine CD9, B. porcine ANXA2, C. porcine B4GALNT2 D. porcine CD46, E. porcine CD59 and F. porcine PROCR have been identified.
Figure 5:
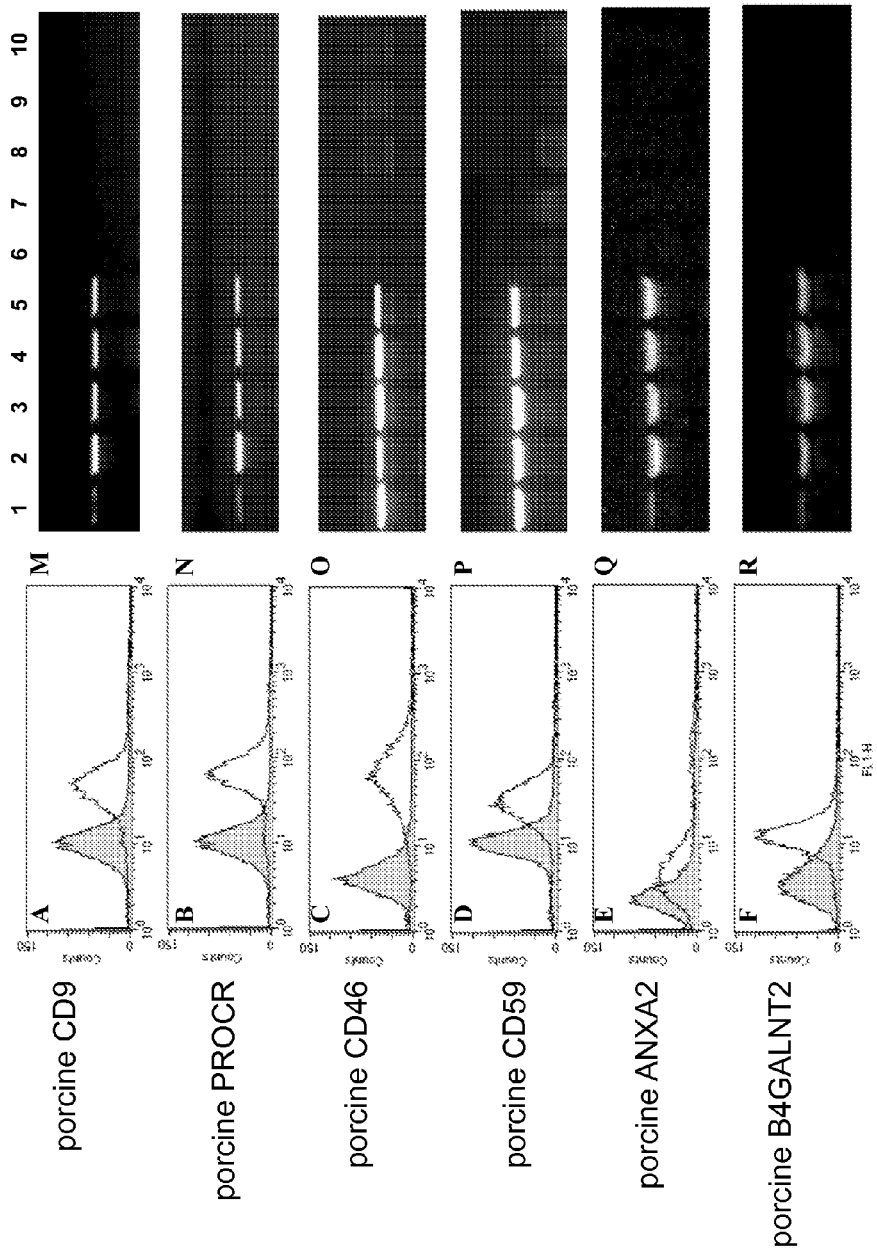
FIG. 5. Analysis of HEK cell lines transformed with pcDNA3.1 vector (Invitrogen) containing individual non-Gal antigen cDNA from pRETRO-PAEC infected isolates. Each stable cell line was screened with sensitized sera. A-F: Flow cytometry profiles of stable cell lines expressing A. porcine CD9, B. porcine PROCR, C. porcine CD46, D. porcine CD59, D; E. porcine ANXA2 and F. porcine B4GALNT2. G-L: Reverse transcriptase PCR analysis for RNA expression of E. porcine CD9, F. porcine PROCR, G. porcine CD46, H. porcine CD59, K. porcine ANXA2 and L. porcine B4GALNT2. Lanes 1-7 are RT-PCR products amplified from lane 1. pig heart, lane 2. PAEC, lanes 3-5. independent HEK transformants containing the nucleotide sequence for each respective non-Gal antigen, lane 6. untransformed HEK cells, lane 7. Flow cytometry negative HEK transformant for each respective non-Gal antigen, and lanes 8-10 are the same as lanes 3-5, however no RT-PCR was performed. These negative controls show that the products in lanes 3-5 are derived from RNA and not genomic DNA.

A standard cDNA expression library was produced using mRNA from GT-positive and GTKO porcine aortic endothelial cells. This library (pRETRO-PAEC) was made in the pRetro-LIB vector (Clontech, FIG. 2A) and was co-transfected with pVSV-G (encoding an envelope glycoprotein from the vesicular stomatitis virus) into GP2-293 packaging cells to produce a pantropic high titer retroviral library stock. The pRETRO-PAEC viral stock was used to infect HEK cells, which were stained with sensitized serum from a pig-to-primate cardiac xenograft recipient 48 hours after infection and then sorted by flow cytometry to collect the brightest 10-30 percent of the cells (FIG. 2B). These bright cells were regrown for 48-72 hours before being selected again. A total of 3-7 rounds of selection were performed, to enrich the population with cells that bound sensitized IgG, prior to isolation of individual cells by flow cytometry. Individual clones were then rescreened for antibody binding (FIG. 2C) and the cDNA insert from antibody positive clones was recovered by PCR amplification of genomic DNA (FIG. 2D) using primers that flank the multiple cloning site of the vector. The amplified product was cloned into a TA-cloning vector (Invitrogen) for sequencing. The sequence of the cDNA insert was used for a BLAST search of the NCBI GenBank database to identify the encoded gene. FIG. 3 lists the results of that BLAST search, showing the species of origin, the common gene names, gene symbol, NCBI reference identification and gene identification number for each of six non-Gal proteins identified in the library screen. For four of these non-Gal polypeptides (CD46, CD59, CD9 and ANXA2) the corresponding pig gene was already identified. In two instances the pig gene had not been previously reported so a bovine homologue, which showed the highest degree of homology, is listed (PROCR and B4GALNT2). A summary of the flow cytometry profile for each of these non-Gal expressing pRETRO-PAEC infected HEK cell lines is presented in FIG. 4.

The pRETRO-PAEC infected HEK cells have a possibility of being infected with more than one virus and may express more than one porcine cDNA. To insure that the identified non-Gal target antigens are the authentic targets of the induced antibody response, each of the non-Gal cDNAs was individually cloned into pcDNA3.1/V5-His-TOPO (Clontech) and transfected into HEK cells. These HEK transformants were selected for G418 resistance and a stable cell line for each non-Gal antigen was produced. These stable cell lines were rescreened with sensitized sera to validate that an induced antibody response was directed towards each of the non-Gal antigens (FIG. 5A-F). Further, RNA samples from porcine hearts and cultured endothelial cells were used to confirm expression of the non-Gal antigens in the transformed HEK cells (FIG. 5G-L) by reverse transcriptase PCR using non-Gal antigen nucleotide sequence specific primers. Antibody to most of the polypeptide non-Gal antigens identified can initiate delayed xenograft rejection through antibody directed complement mediated injury to the vascular endothelial cells but can also exacerbate delayed xenograft rejection by blocking the normal functions of these proteins (CD46, CD59, CD9, porcine PROCR and ANXA2). Both CD46 and CD59 are known as complement regulatory proteins (CRPs). These membrane proteins are widely expressed and normally function to limit complement mediated damage to autologous cells. Because they are membrane proteins, they act locally on the cell surface and establish an intrinsic barrier to complement mediated damage. They do not systemically deplete complement. CD46 is a cofactor for complement factor I and functions to cleave surface bound C3b and C4b to block a key amplification step in the complement cascade and CD59 blocks the polymerization of the membrane attack complex, the terminal step in complement activation which leads to cell lysis. In xenotransplantation, the use of human CRP transgenes (CD46, CD55 and CD59) has been central to endowing donor organs with greater resistance to complement mediated damage. It was initially believed that human and porcine CRPs acted in an essentially species specific fashion, with the CRPs of each species being effective only against complement of the autologous species. While some aspect of this may be true, it is also clear that enhanced expression of CRP function, even porcine CRPs, will act to limit primate complement induced damage. Antibody responses to these porcine CRPs may block the function of these proteins and thereby effectively reduce the overall complement regulatory capacity of the organ. Induced antibody to porcine CRPs would place the donor organ at greater risk for antibody directed complement mediated damage.

The polypeptide non-Gal antigen CD9 is a tetraspanin protein family member. These proteins have four hydrophobic transmembrane domains. CD9 has two extracellular protein loops where most of the amino acid variation between species is found. CD9 is well known for its presence on platelets and anti-CD9 antibodies efficiently activate platelets that in some instances can induce a lethal thrombosis. CD9 is also expressed on endothelial cells where it forms tetraspanin enriched microdomains (TEM). Antibodies to CD9 on endothelial cells promote neutrophil adhesion, possibly through endothelial cell activation or by cross linking TEMs to aggregate neutrophil adhesion proteins VCAM and ICAM. In the context of a xenograft, an antibody response to porcine CD9 (on endothelium) promotes neutrophil adhesion and subsequent endothelial cell activation or injury. If the induced anti-CD9 cross reacts with recipient CD9, even to a limited extent, then the antibody might effectively cross link recipient platelets to the endothelium of the xenograft creating a potent thrombogenic effect.

The non-Gal antigen PROCR acts on the endothelial cell surface to enhance the formation of activated protein C by the complex of thrombin and thrombomodulin. Activated protein C is a prominent anticoagulant due to its cleavage of coagulation factors VI and VIIIa which reduce thrombin generation. PROCR can also be shed from the endothelial cell surface by the effects of metalloproteinase. The soluble receptor-activated protein C complex appears to bind to neutrophils and decrease their binding to the endothelium. Anti-inflammatory effects have also been associated with PROCR-activated protein C complex. Antibodies have been isolated which block the function of PROCR (Ye et al., *Biochem Biophys Res Commun,* 259(3):671-677 (1999)). Antibody with this specificity in a xenograft recipient can enhance coagulation and xenograft rejection.

ANXA2 was indentified as a porcine non-Gal endothelial cell membrane antigen (Byrne et al., *Xenotransplantation,* 15: 268-276 (2008)). Annexins are a family of diverse genes which encode proteins with calcium regulated phospholipid and membrane binding functions. The annexins are mainly considered intracellular proteins that act as anchors connecting cytoskeletal elements to the membrane and supporting membrane-membrane interactions. As such, they are implicated in exocytosis, endocytosis and stabilization of organelle and plasma membrane domains. Some annexins, including the identified non-Gal antigen ANXA2, are found on the extracellular surface and have extracellular functions. ANXA2 is an endothelial cell surface receptor for plasminogen and tissue type plasminogen activator (tPA). Consistent with this, ANXA2 knock-out mice show reduced levels of tPA dependent plasmin generation and exhibit incomplete clearance of arterial thrombi (Cockrell et al., *Lupus,* 17(10): 943-951 (2008)). It may be anticipated that extracellular ANXA2 can promote fibrinolysis and may thereby forestall graft rejection by limiting the extent of thrombosis. Anti-ANXA2 antibodies that block the proposed ANXA2 fibrinolytic function could in effect promote thrombosis within the xenograft. Additionally, antibody responses to ANXA2 have been detected in patients with antiphospholipid syndrome and shown to cause endothelial cell activation and the induction of tissue factor which would also contribute to a prothrombotic vasculature (Cesarman-Maus et al., *Blood,* 107(11):4375-4382 (2006)).

The B4GALNT2 enzyme was also identified as a non-Gal antigen in the library screen. The gene for this enzyme has been cloned from humans and mice. The enzyme catalyzes the addition of N-acetylgalactosamine to terminal α2,3-sialylated galactose residues in the β1,4 linkage to produce the Sd$^a$ antigen. There is a 74 percent and 68 percent amino acid identity between the translated porcine polypeptide sequence isolated herein and the human and murine B4GALNT2 polypeptides respectively (FIG. 6). The porcine B4GALNT2 gene is expected to encode a polypeptide with similar, though not necessarily identical, enzymatic activity as seen for the human and murine sequences. The Sd$^a$ antigen, also known as CAD, is expressed on 90 percent of Caucasian red blood cells, in human urine as the Tamm-Horsfall glycoprotein, in the oxyntic mucosa of the stomach as a glycolipid and in the colonic mucosa as a glycoprotein. The *Dolichos biflorus* lectin (DBA) can be used to detect the Sd$^a$ antigen by binding to the β-linked N-acetylgalactosamine (Kamada et al., *J Biochem,* 109(1):178-183 (1991); Piller et al., *European journal of biochemistry/ FEBS,* 191(2):461-466 (1990). The DBA lectin binds poorly to HEK cells but shows increased binding to HEK cells infected with the pRETRO vector expressing porcine B4GALNT2 (FIG. 7A). There is a high level of DBA binding to porcine aortic endothelial cells but minimal binding to baboon aortic endothelial cells (FIGS. 7B and C). Likewise, lectin staining of porcine and baboon heart samples show a high level of DBA binding to porcine endothelium with little if any binding to baboon heart (FIGS. 7D and E). This is consistent with previous DBA staining of porcine femoral arteries and microvascular endothelial cells (Solanes et al., *Anatomia, histologia, embryologia,* 34(2): 105-111 (2005); Johnson et al., *Microvascular research,* 64(2):278-288 (2002)). Alloantibodies to the Sd$^a$ antigen have been noted at low frequency in military veterans and an induced response to Sd$^a$ has been observed in some patients after transfusion (Tormey et al., *Transfusion,* 48(10):2069-2076 (2008); Spitalnik et al., *Vox Sang,* 42(6):308-312 (1982)). The identification of the B4GALNT2 cDNA nucleotide sequence in the library screen suggests that an anti-Sd$^a$ or antibody response to an Sd$^a$-like carbohydrate on the xenograft may be present in non-human primates.

Example 2

Engineering a Targeted Disruption in the Porcine B4GALNT2 Nucleotide Sequence

The cDNA sequence of porcine B4GALNT2 and its conservation in human and mouse provides the needed information to design a targeting vector suitable for disrupting the porcine B4GALNT2 gene using the standard methods of homologous recombination. The amino acids encoded by the nucleotides of individual exons in the human and murine genes show conservation (FIG. 6). This is a common observation in mammalian genes when exons from different species encode the same or similar portions of a polypeptide. This conservation suggests that the porcine B4GALNT2 gene is made up of 11 coding exons and suggests the approximate location for exon boundaries within the porcine cDNA.

The porcine, human and murine B4GALNT2 cDNA sequences exhibit a high level of conservation in the region that encodes the C-terminal portion of the polypeptide. This region of the human B4GALNT2 cDNA sequence encodes a portion of the B4GALNT2 polypeptide that is important for enzymatic activity (Montiel et al., *Biochem J.,* 373:369-379 (2003)). This is likely to be similar in the porcine B4GALNT2 polypeptide based on conservation. This region is also conserved by the related human GM2 synthase that encodes an N-acetylgalactosamine transferase polypeptide. Human GM2 and human, murine and porcine B4GALNT2 share a conserved amino acid sequence (SQVTTKYVL-WVDDDF (SEQ ID NO:7)) encoded by exon 9 (boldface in FIG. 6). Within this sequence is an acidic DXD motif (underlined) that is conserved in 13 glycosyltransferase families of the CAZy classification and is required for GM2 enzymatic activity (Li et al., *Glycobiology,* 11:217-229 (2001)). This suggests that the amino acids encoded by exon 9 in the human and murine B4GALNT nucleotide sequences are involved in the catalytic site and that the corresponding porcine amino acid sequence will have a similar function. The putative exons 9 and 10 of the porcine B4GALNT2 nucleotide sequence were deleted in the construct. The loss of such sequences, that include the conserved sequence associated with the enzymatic active site, should effectively eliminate the function of the gene.

Figure 10B:
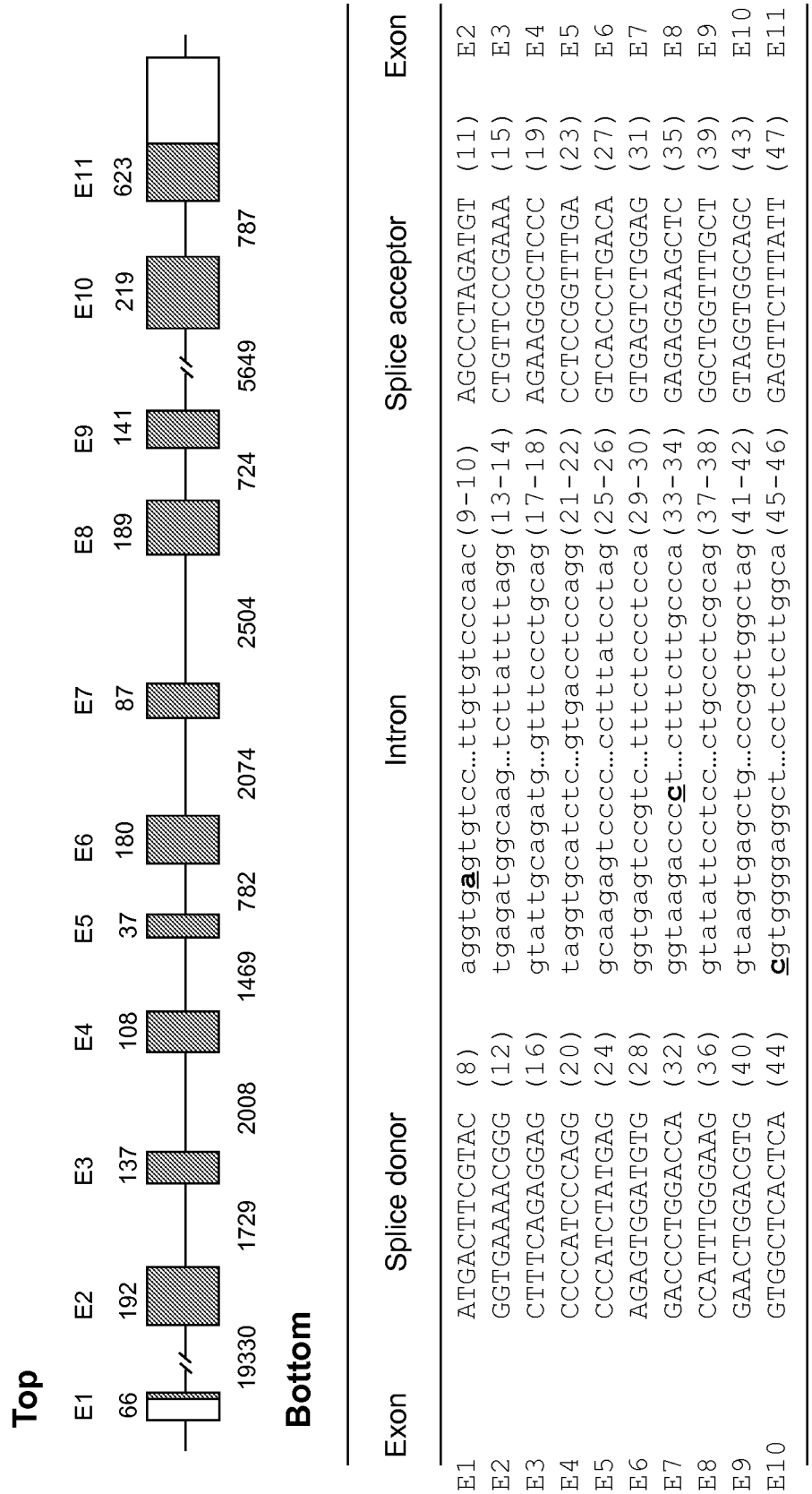
FIG. 10B. Top panel is a schematic diagram of the genomic organization of the pig B4GALNT2 gene. Bottom panel contains the exon-intron junction sequences of the pig B4GALNT2 gene. Sequence identifiers are in parentheses.

To design a targeting vector suitable for disrupting the porcine B4GALNT2 gene requires 200-1000 basepairs of homologous porcine sequences that flank the targeted neomycin insertion site. These sequences cannot come directly from the B4GALNT2 cDNA as mammalian genes are composed of a series of highly dispersed exons which are spliced together to produce the cDNA. Instead genomic DNA that immediately flanks the desired insertion site must be used. Based on the conserved exon encoded portions of the B4GALNT2 protein in humans and mice, the porcine gene likely consists of 11 coding exons encoding approximately 5, 63, 46, 35, 13, 60, 29, 63, 47, 73, and 69 amino acids each in that order (FIG. 8). To isolate genomic DNA flanking the enzymatic active site we designed PCR primers (FIG. 8), based on the conserved exon protein relationships exhibited by human and murine B4GALNT. These primers amplify the porcine genomic DNA between the presumed exons 8 and 9 and exons 10 and 11 of the porcine B4GALNT gene (FIG. 8). The porcine genomic PCR products were sequenced (FIGS. 9 and 10). Each shows the known primer sequence, and an adjacent 14-47 nucleotides of porcine B4GALNT2 coding sequence. This confirms that the PCR products are derived from the porcine B4GALNT gene and that the intervening sequences represent authentic intron sequences of the porcine B4GALNT2 gene. These introns would correspond to the homologous introns 8 and 10 based on the structure of the human and mouse genes. This strategy has been repeated for all of the intron and exon boundaries for the porcine B4GALNT2 gene, confirming the presence of 11 coding exons and providing essential noncoding genomic sequences for isolating any combination of intron and exons (FIG. 10B).

Figure 11:
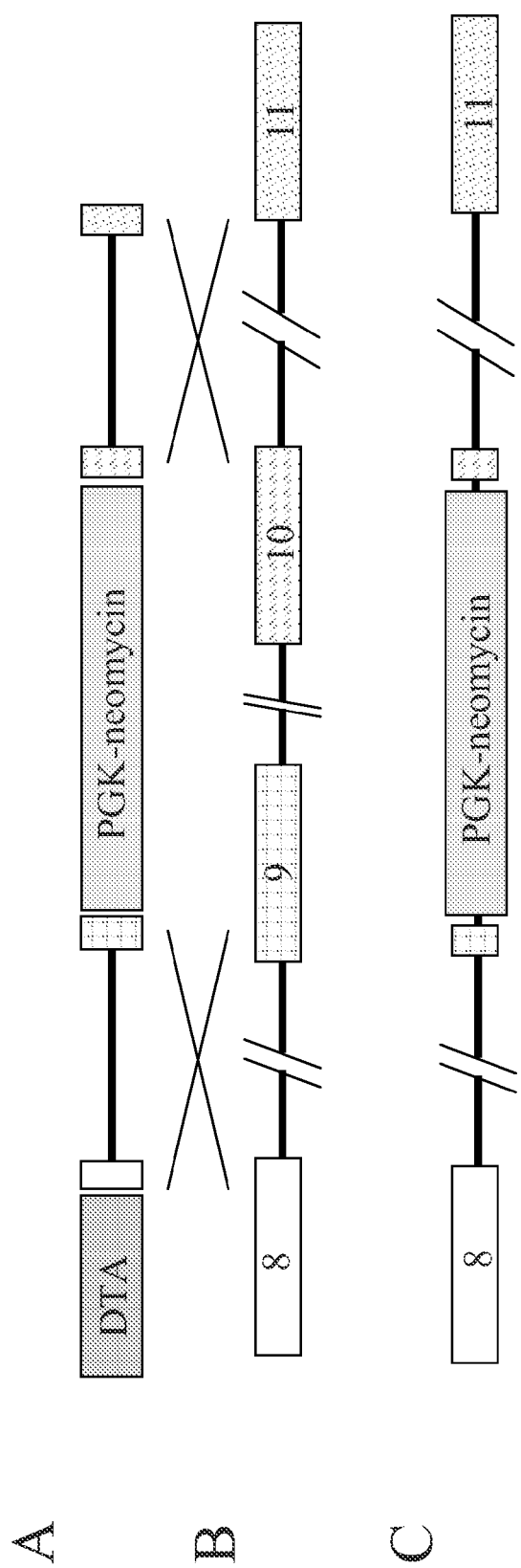
FIG. 11. Targeting vector for disruption of endogenous porcine B4GALNT nucleotide sequence. Illustration of the A. targeting vector, B. putative genomic structure of the porcine B4GALNT2 gene and C. resulting product produced after homologous recombination. Hash marks between A and B indicate regions of homologous recombination which result in the structure depicted in C. DTA is a polymerase 2 regulated diptheria toxin for negative selection. PGK-neomycin is a PGK regulated neomycin selectable marker. Numbers refer to putative exon structure of the porcine B4GALNT2 gene. These numbers are based on homology to the human and murine genes.

The intron 8 and intron 10 PCR products provide the homologous genomic sequences needed to produce a targeting vector to disrupt the B4GALNT2 gene in a manner analogous to the process used to disrupt the GGTA-1 locus (Sharma et al., *Transplantation,* 75:430-436 (2003). This vector would consist of the following components; a polymerase 2 regulated diphtheria toxin A gene (DTA), 5' flanking homologous sequences including portions of the porcine B4GALNT2 coding sequences and the intron 8 sequence, a PGK-neomycin resistance cassette and 3' flanking homologous sequences including portions of the porcine B4GALNT2 coding sequence and the intron 10 sequence (FIG. 11). The DTA gene provides a negative selectable marker to minimize the frequency of non-homologous insertions. Homologous recombination events within the 5' and 3' flanking sequences result in a loss of the DTA and an insertion of the PGK-Neo marker. This PGK-Neo insertion effectively deletes most of the coding sequence encoded by putative exons 9 and 10 of the porcine B4GALNT2 gene. The loss of these sequences, which would include the conserved sequence associated with the enzymatic active site and the insertion of the PGK-Neo gene would effectively eliminate the function of the gene. The construct could further include frame shift alterations and in frame termination codons to further insure disruption of the B4GALNT2 gene.

Example 3

Monitoring the Progress of Pig Heart Xenograft Rejection

Figure 12:
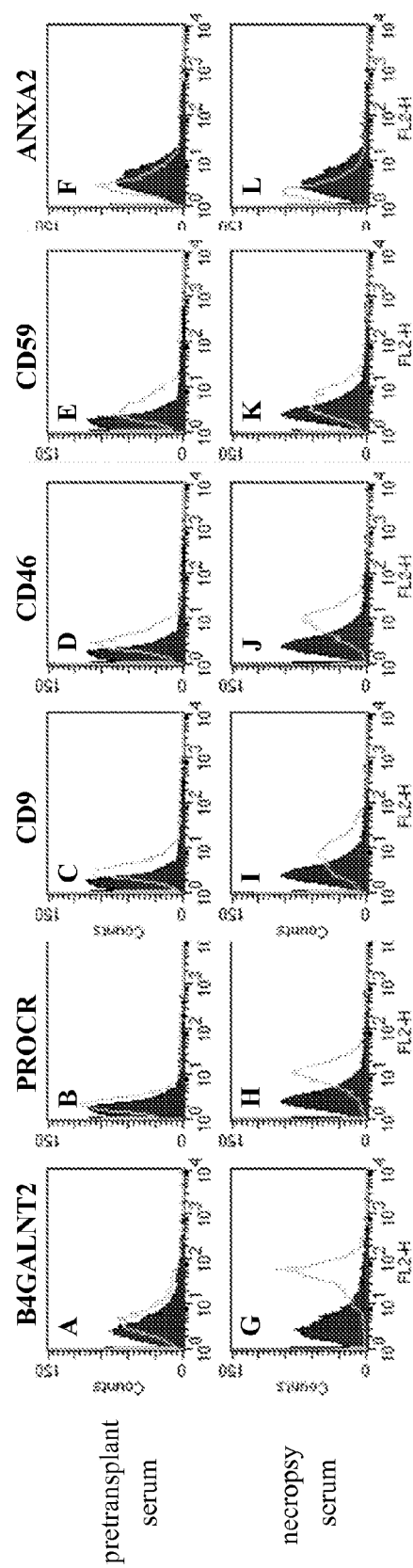
FIG. 12. Using non-Gal antigen expressing HEK cell lines to detect induced non-Gal antibody. Screening non-Gal immune responses using HEK transformed cells expressing non-Gal antigens. A cDNA for each of the non-Gal antigens in FIG. 3 was cloned into the mammalian expression vector pcDNA3.1/V5-His-TOPO. HEK cell lines expressing each of these cDNAs were incubated with pretransplant and necropsy serum (diluted 1:40) from a non-immunosuppressed heterotopic cardiac xenograft recipient and antibody binding was detected using a FITC conjugated anti-human IgG. Flow cytometry was used to determine the antibody response to each of the antigens. Panels A-F are pretransplant serum. Panels G-L are necropsy serum. The antigen expressed by the HEK cell line is listed above the pretransplant/necropsy serum pairs (A. and G. B4GALNT2, B. and H. PROCR, C. and I. CD9, D. and J. CD46, E. and K. CD59, F. and L. ANXA2). Specific staining is the thin line. Background staining is IgG binding to a G418 resistant HEK cell line transfected with the pcDNA3.1V/5-His-TOPO vector lacking an insert.
Figure 13:
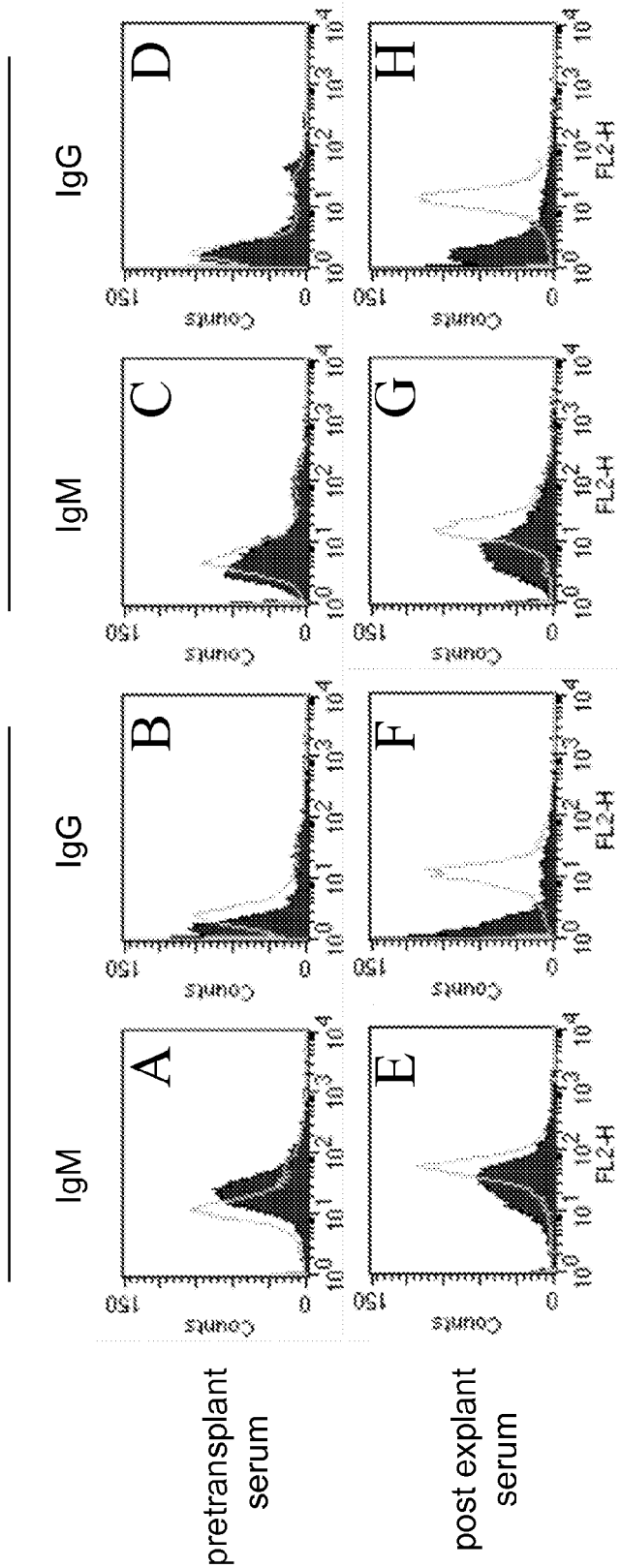
FIG. 13. Monitoring antibody responses to the $Sd^a$-like antigen response encoded by porcine B4GALNT2 expressed by the HEK-B4GALNT2 cell line. A-D. pretransplant and E-H. post explant serum reactivity to the HEK-B4GALNT2 cell line of GTKO heterotopic cardiac xenograft recipients. IgM (A and E) and IgG (B and F) reactivity is shown for a recipient that rejected the GTKO cardiac xenograft on day 27. IgM (C and G) and IgG (D and H) reactivity is shown for a recipient that rejected the GTKO cardiac xenograft on day 22. Background staining (filled) is serum reactivity to a G418 resistant HEK cell line transfected with pcDNA3.1/V5-His-TOPO vector without an insert. The transplants were performed under full immunosuppression as described in Byrne et al., *Xenotransplantation*, 15:268-276 (2008).

Utilizing cDNAs encoding the polypeptide non-Gal antigens identified herein, HEK cell lines were developed expressing each of the polypeptide non-Gal antigens with the exception of B4GALNT2. These cell lines were directly used to monitor non-Gal antibody responses to individual non-Gal antigens (i.e. CD46, CD59, CD9, PROCR and ANXA2). Stable HEK cell lines expressing each of these cDNAs were incubated with pre-transplant and necropsy serum (diluted 1:40) from a non-immunosuppressed heterotopic cardiac xenograft recipient. Antibody binding was detected using a FITC conjugated anti-human IgG. Flow cytometry was used to determine the antibody response to each of the antigens (FIG. 12). The xenograft recipient had a strongly induced antibody response to the B4GALNT2 antigen and PROCR, a less intense though positive response to porcine CD9 and CD46 and a minimal response to porcine CD59 and ANXA2. This same strategy can be used for any porcine xenograft recipient and is not limited to non-immunosuppressed recipients. FIG. 13 illustrates the induced antibody response to the B4GALNT2 antigen in two GTKO pig to primate recipients which were fully immunosuppressed. In each case a weak induction of IgM and a stronger induction of B4GALNT2 reactive IgG was detected.

Example 4

Glycan Array Analysis

The HEK-B4GALNT2 cell line, identified in a library screen, expresses a porcine glycosyltransferase similar to B4GALNT2 in humans and mice (FIG. 6). The murine and human B4GALNT2 transferase can add N-acetylgalactosamine to galactose containing an alpha 2, 3 sialic acid residue. This results in formation of the SDa glycan. In the HEK-B4GALNT2 cells, expression of the porcine B4GALNT2 gene leads to formation of a new non-Gal glycan, not present on normal HEK cells, which is the target of an induced antibody response after pig-to-primate xenotransplantation. The sequence homology shared between the porcine glycosyltransferase and the human and mouse B4GALNT2 genes (FIG. 6) suggests that the porcine gene is likely to perform a similar enzymatic function resulting in expression of an SDa or SDa-like glycan on the surface of the HEK-B4GALNT2 cells. This suggests that an SDa or SDa-like glycan can be a new non-Gal carbohydrate antigen, however, the precise enzymatic function of the porcine gene product is not known and variation in the protein sequence may alter its enzymatic activity compared to the human and murine genes. Furthermore, expression of porcine B4GALNT2 in HEK cells can compete with endogenous glycosyltransferases and may alter the glycan composition.

A mammalian printed glycan array (Version 4.2) produced by the Consortium of Functional Glycomics, directed by James Paulson, Department of Chemical Physiology, Scripps Institute, (World Wide Web at "functionalglycomics.org/static/consortium/organization.shtml") was used to measure the anti-glycan specificity present in post-transplant sensitized primate serum as a means of further defining the glycans present on HEK-B4GALNT2 cells. Glycan arrays are similar to those described elsewhere (Wong et al., *Curr. Opin. Chem. Biol.*, 12:86-92 (2008) and Paulson et al., *Nature Chem. Biol.*, 2(5):238-248 (2006)).

Figure 7:
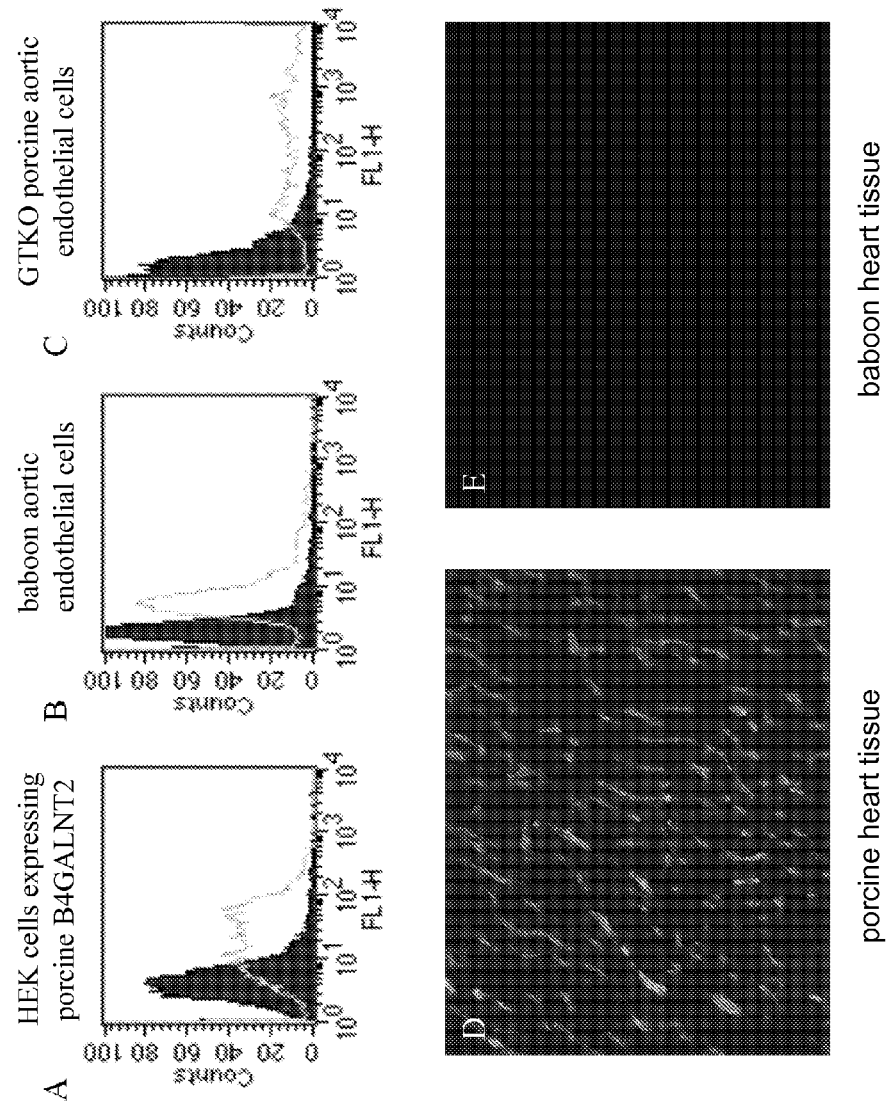
FIG. 7. Analysis of fluorescein isothiocyanate (FITC) conjugated *Dolichos biflorus* lectin (DBA) binding. A. DBA binding to HEK cells (filled) and HEK cells infected with a pRETRO virus expressing porcine B4GALNT2 (line). B. DBA binding to baboon aortic endothelial cells (thin line). The filled histogram is unstained baboon endothelial cells. C. DBA binding to GTKO porcine aortic endothelial cells (line). The filled histogram is unstained porcine endothelial cells. D. and E. show FITC-DBA staining of porcine and baboon heart tissue, respectively.
Figure 14:
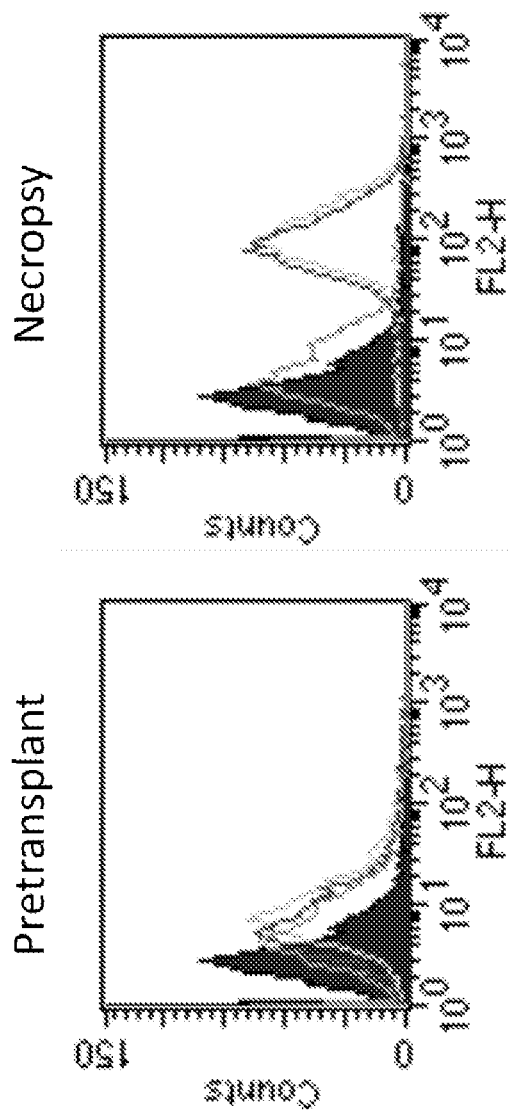
FIG. 14. Flow cytometry analysis of pre-transplant and sensitized necropsy serum IgG binding to HEK-B4GALNT2 cells. Each panel shows IgG binding to HEK-B4GALNT2 cells without absorption (labeled "g") after repeated absorption with HEK cells labeled "r") and after further repeated absorption with HEK-B4GALNT2 cells labeled "b"). The IgG binding present in necropsy serum is specific for a glycan encoded by porcine B4GALNT2, and uniquely present on HEK-B4GALNT2 cells, as absorption with HEK cells did not substantially affect IgG binding (compare "g" and "r" histograms)), but absorption with HEK-B4GALNT2 cells reduced IgG binding to back ground levels ("b" histogram). For absorption of the serum the pretransplant and necropsy serum samples (diluted 1:10) were incubated with $10^7$ HEK cells at 4° C. for 60 minutes. After incubation the cells were removed by centrifugation and the serum recovered. Each serum sample was absorbed three times. A portion of the HEK absorbed serum was then subsequently absorbed three times against $10^7$ HEK-B4GALNT2 cells. Background staining (filled histogram) is binding of the secondary PE-conjugated anti-human IgG only.

Pretransplant and sensitized necropsy serum from a GTKO pig-to-primate cardiac xenograft recipient contained, in addition to other non-Gal specificities, a high level of HEK-B4GALNT2 reactivity (FIG. 14). This reactivity was specific for the glycan produced by expression of porcine B4GALNT2 and uniquely present on HEK-B4GALNT2 cells as absorption of the sensitized serum with HEK cells did not diminish IgG binding to HEK-B4GALNT2 cells whereas absorption with HEK-B4GALNT2 cells reduced IgG binding to background levels. These serum sources were used to probe the mammalian glycan array to identify glycan structures with increased IgG binding in the sensitized necropsy serum (FIGS. 15A and B). The identified structures included the SDa antigen (structure 389) and oligosaccharides containing N-Acetylneuraminic acid substitutions or N-Acetylgalactosamine residues. These structures are broadly compatible with the presumed activity of the porcine B4GALNT2 gene and with the lectin DBA binding detected on porcine endothelial cells and on HEK-B4GALNT2 cells (FIG. 7). When necropsy serum was absorbed with HEK-B4GALNT2 cells, reactivity to these glycans was reduced (FIG. 15C) by 20-70%, suggesting that these, or similar structures, are present on the HEK-B4GALNT2 surface.

While the glycan array data were largely qualitative, the structures identified in FIG. 15 may be present on the surface of HEK-B4GALNT2 cells, but there may be additional related structures which were not detected in this analysis and may contribute to the reduction in IgG binding after absorption. Also the porcine B4GALNT2 enzyme may act directly to produce a certain structure, such as SDa, but it may also act indirectly, through competitive interaction with other glycosyltransferases present in HEK cells, to produce increased levels of other oligosaccharides which may also contribute to non-Gal IgG binding to these cells. For these reasons, this analysis is not an exhaustive enumeration of the oligosaccharides produced by porcine B4GALNT2 or oligosaccharides that may contribute to non-gal IgG binding to this cell line.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for providing a primate with a cardiac xenograft, said method comprising implanting said cardiac xenograft into said primate, wherein said xenograft is from a transgenic pig whose genome comprises disrupted β1,4 N-acetyl-galactosaminyl transferase 2 (B4GALNT2) nucleotide sequences and disrupted α-1-3 galactosyl transferase (GT) glycosyltransferase nucleotide sequences, wherein said xenograft has at least 50 percent less expression of a-Gal antigen as compared to the level of a-Gal antigen expression by a control, non-transgenic pig, and wherein said xenograft has at least 50 percent less expression of an $Sd^a$ antigen as compared to the level of $Sd^a$ antigen expression by a control, non-transgenic pig, wherein said xenograft exhibits reduced immunogenicity when implanted into said primate as compared to a cardiac xenograft from a wild-type pig, and wherein the primate is immunosuppressed.

2. A method for providing a primate with a cardiac xenograft, said method comprising implanting said cardiac xenograft into said primate, wherein said xenograft is from a transgenic pig whose genome comprises disrupted β1,4

N-acetyl-galactosaminyl transferase 2 (B4GALNT2) nucleotide sequences and disrupted α-1-3 galactosyl transferase (GT) glycosyltransferase nucleotide sequences, wherein said xenograft has no expression of an a-Gal antigen, and wherein said xenograft has no expression of an $Sd^a$ antigen on endothelial cell membranes, wherein said xenograft exhibits reduced immunogenicity when implanted into said primate as compared to a cardiac xenograft from a wild-type pig, and wherein the primate is immunosuppressed.

3. A method for providing a primate with a cardiac xenograft, said method comprising implanting said cardiac xenograft into said primate, wherein said xenograft was obtained from a transgenic pig whose genome comprises disrupted β1,4 N-acetyl-galactosaminyl transferase 2 (B4GALNT2) nucleotide sequences and disrupted α-1-3 galactosyl transferase (GT) glycosyltransferase nucleotide sequences, wherein said xenograft comprises no detectable B4GALNT2 activity and no detectable GT activity, wherein said xenograft exhibits reduced immunogenicity when implanted into said primate as compared to a cardiac xenograft from a wild-type pig, and wherein the primate is immunosuppressed.

* * * * *

UNITED STATES PATENT AND TRADEMARK OFFICE
CERTIFICATE OF CORRECTION

PATENT NO. : 9,642,899 B2  
APPLICATION NO. : 13/696478  
DATED : May 9, 2017  
INVENTOR(S) : Christopher G. A. McGregor and Guerard W. Byrne Page 1 of 1

It is certified that error appears in the above-identified patent and that said Letters Patent is hereby corrected as shown below:

On the Title Page

Column 1, Line 10, after "U.S.C." insert -- § --, therefor;

In the Claims

Column 37, Line 66 (Claim 1, first occurrence), please delete "a-Gal" and insert -- α-Gal --, therefor;

Column 37, Line 66 (Claim 1, second occurrence), please delete "a-Gal" and insert -- α-Gal --, therefor;

Column 39, Line 4 (Claim 2), please delete "a-Gal" and insert -- α-Gal --, therefor.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 47

<210> SEQ ID NO 1
<211> LENGTH: 503
<212> TYPE: PRT
```

<213> ORGANISM: Sus scrofa

<400> SEQUENCE: 1

```
Met Thr Ser Tyr Ser Pro Arg Cys Leu Ser Ile Leu Lys Ile Leu Met
 1               5                  10                  15
Val Leu Leu Val Leu Ser Val Gly Leu Phe Met Phe Gln Ser Val Phe
            20                  25                  30
Leu Asp Thr Asp Phe Ser Leu Leu Asn Ser Pro Ile Pro Ser Pro Thr
        35                  40                  45
Leu Asp Ala Gln Thr Leu Lys Leu Leu Pro Glu Lys Pro Asp Phe Tyr
    50                  55                  60
Gly Glu Asn Gly Leu Phe Ser Lys Asn Gln Cys Gln Cys Asp Ala Phe
65                  70                  75                  80
Gly His Gln Glu Ser Tyr Asn Leu Glu Asp Ala Tyr Asp Pro Gln Asp
                85                  90                  95
Leu Pro Ala Val Asn Leu Arg Arg Gln Ala Glu Leu Glu His Phe Gln
            100                 105                 110
Arg Arg Glu Gly Leu Pro Arg Pro Pro Leu Leu Ala Gln Pro Asn
        115                 120                 125
Leu Pro Phe Gly Tyr Pro Val His Gly Val Glu Val Met Pro Leu His
    130                 135                 140
Thr Ile Pro Ile Pro Gly Leu Arg Phe Glu Gly Pro Asp Ala Pro Ile
145                 150                 155                 160
Tyr Glu Val Thr Leu Thr Ala Ser Leu Gly Thr Leu Asn Ala Leu Ala
                165                 170                 175
Asp Val Pro Asp Asn Val Val Arg Gly Arg Gly Gln Lys Gln Leu Asn
            180                 185                 190
Ile Leu Thr Ser Ser Arg Glu Leu Leu Asn Phe Ile Leu Gln His Val
        195                 200                 205
Thr Tyr Thr Ser Thr Glu Tyr His Leu His Arg Val Asp Val Val Ser
    210                 215                 220
Leu Glu Ser Lys Ser Ser Val Ala Lys Phe Pro Val Thr Ile Arg Tyr
225                 230                 235                 240
Pro Val Met Pro Lys Leu Tyr Asp Pro Gly Pro Glu Arg Lys Leu Arg
                245                 250                 255
Asp Leu Val Thr Ile Ala Thr Lys Thr Phe Leu Arg Pro His Lys Leu
            260                 265                 270
Met Thr Met Leu Arg Ser Val Arg Glu Tyr Tyr Pro Asp Leu Thr Val
        275                 280                 285
Ile Val Ala Asp Asp Ser Lys Glu Pro Leu Lys Ile Thr Asp Ser His
    290                 295                 300
Val Glu Tyr Tyr Thr Met Pro Phe Gly Lys Gly Trp Phe Ala Gly Arg
305                 310                 315                 320
Asn Leu Ala Ile Ser Gln Val Thr Thr Lys Tyr Val Leu Trp Val Asp
                325                 330                 335
Asp Asp Phe Ile Phe Asn Ser Lys Thr Arg Ile Glu Ala Leu Ala Asp
            340                 345                 350
Val Leu Glu Lys Thr Glu Leu Asp Val Val Gly Gly Ser Val Ile Glu
        355                 360                 365
Asn Thr Phe Gln Phe Lys Leu Leu Glu Gln Gly Lys Asn Gly Asp
    370                 375                 380
Cys Leu His Gln Gln Pro Gly Phe Phe Arg Pro Val Asp Gly Phe Pro
385                 390                 395                 400
```

```
Asp Cys Val Val Thr Ser Gly Val Val Ser Phe Phe Leu Ala His Thr
                405                 410                 415

Glu Arg Leu Gln Arg Ile Gly Phe Asp Pro Arg Leu Gln Arg Val Ala
        420                 425                 430

His Ser Glu Phe Phe Ile Asp Gly Leu Gly Ser Leu Leu Val Gly Ser
        435                 440                 445

Cys Pro His Val Ile Ile Gly His Gln Pro His Leu Pro Val Met Asp
        450                 455                 460

Pro Glu Leu Ala Thr Leu Glu Gly Asn Tyr Thr Ser Tyr Arg Ala Asn
465                 470                 475                 480

Thr Glu Ala Gln Ile Lys Phe Lys Leu Ala Leu His Tyr Phe Lys Asn
                485                 490                 495

Tyr Leu Gln Cys Ala Thr Asn
                500

<210> SEQ ID NO 2
<211> LENGTH: 509
<212> TYPE: PRT
<213> ORGANISM: Homo sapiens

<400> SEQUENCE: 2

Met Thr Ser Gly Gly Ser Arg Phe Leu Trp Leu Leu Lys Ile Leu Val
 1               5                  10                  15

Ile Ile Leu Val Leu Gly Ile Val Gly Phe Met Phe Gly Ser Met Phe
                20                  25                  30

Leu Gln Ala Val Phe Ser Ser Pro Lys Pro Glu Leu Pro Ser Pro Ala
        35                  40                  45

Pro Gly Val Gln Lys Leu Lys Leu Leu Pro Glu Glu Arg Leu Arg Asn
 50                 55                  60

Leu Phe Ser Tyr Asp Gly Ile Trp Leu Phe Pro Lys Asn Gln Cys Lys
65                  70                  75                  80

Cys Glu Ala Asn Lys Glu Gln Gly Gly Tyr Asn Phe Gln Asp Ala Tyr
                85                  90                  95

Gly Gln Ser Asp Leu Pro Ala Val Lys Ala Arg Arg Gln Ala Glu Phe
            100                 105                 110

Glu His Phe Gln Arg Arg Glu Gly Leu Pro Arg Pro Leu Pro Leu Leu
            115                 120                 125

Val Gln Pro Asn Leu Pro Phe Gly Tyr Pro Val His Gly Val Glu Val
        130                 135                 140

Met Pro Leu His Thr Val Pro Ile Pro Gly Leu Gln Phe Glu Gly Pro
145                 150                 155                 160

Asp Ala Pro Val Tyr Glu Val Thr Leu Thr Ala Ser Leu Gly Thr Leu
                165                 170                 175

Asn Thr Leu Ala Asp Val Pro Asp Ser Val Val Gln Gly Arg Gly Gln
            180                 185                 190

Lys Gln Leu Ile Ile Ser Thr Ser Asp Arg Lys Leu Leu Lys Phe Ile
        195                 200                 205

Leu Gln His Val Thr Tyr Thr Ser Thr Gly Tyr Gln His Gln Lys Val
        210                 215                 220

Asp Ile Val Ser Leu Glu Ser Arg Ser Ser Val Ala Lys Phe Pro Val
225                 230                 235                 240

Thr Ile Arg His Pro Val Ile Pro Lys Leu Tyr Asp Pro Gly Pro Glu
                245                 250                 255

Arg Lys Leu Arg Asn Leu Val Thr Ile Ala Thr Lys Thr Phe Leu Arg
            260                 265                 270
```

```
Pro His Lys Leu Met Ile Met Leu Arg Ser Ile Arg Glu Tyr Tyr Pro
        275                 280                 285

Asp Leu Thr Val Ile Val Ala Asp Ser Gln Lys Pro Leu Glu Ile
    290                 295                 300

Lys Asp Asn His Val Glu Tyr Tyr Thr Met Pro Phe Gly Lys Gly Trp
305                 310                 315                 320

Phe Ala Gly Arg Asn Leu Ala Ile Ser Gln Val Thr Thr Lys Tyr Val
                325                 330                 335

Leu Trp Val Asp Asp Asp Phe Leu Phe Asn Glu Glu Thr Lys Ile Glu
                340                 345                 350

Val Leu Val Asp Val Leu Glu Lys Thr Glu Leu Asp Val Val Gly Gly
                355                 360                 365

Ser Val Leu Gly Asn Val Phe Gln Phe Lys Leu Leu Leu Glu Gln Ser
    370                 375                 380

Glu Asn Gly Ala Cys Leu His Lys Arg Met Gly Phe Phe Gln Pro Leu
385                 390                 395                 400

Asp Gly Phe Pro Ser Cys Val Val Thr Ser Gly Val Val Asn Phe Phe
                405                 410                 415

Leu Ala His Thr Glu Arg Leu Gln Arg Val Gly Phe Asp Pro Arg Leu
                420                 425                 430

Gln Arg Val Ala His Ser Glu Phe Phe Ile Asp Gly Leu Gly Thr Leu
                435                 440                 445

Leu Val Gly Ser Cys Pro Glu Val Ile Ile Gly His Gln Ser Arg Ser
    450                 455                 460

Pro Val Val Asp Ser Glu Leu Ala Ala Leu Glu Lys Thr Tyr Asn Thr
465                 470                 475                 480

Tyr Arg Ser Asn Thr Leu Thr Arg Val Gln Phe Lys Leu Ala Leu His
                485                 490                 495

Tyr Phe Lys Asn His Leu Gln Cys Ala Ala Asn Arg Cys
                500                 505

<210> SEQ ID NO 3
<211> LENGTH: 511
<212> TYPE: PRT
<213> ORGANISM: Mus musculus

<400> SEQUENCE: 3

Met Thr Ser Ser Val Ser Phe Ala Ser Phe Arg Phe Pro Trp Leu Leu
  1               5                  10                  15

Lys Thr Phe Val Leu Met Val Gly Leu Ala Thr Val Ala Phe Met Val
                20                  25                  30

Arg Lys Val Ser Leu Thr Thr Asp Phe Ser Thr Phe Lys Pro Lys Phe
            35                  40                  45

Pro Glu Pro Ala Arg Val Asp Pro Val Leu Lys Leu Leu Pro Glu Glu
 50                  55                  60

His Leu Arg Lys Leu Phe Thr Tyr Ser Asp Ile Trp Leu Phe Pro Lys
 65                  70                  75                  80

Asn Gln Cys Asp Cys Asn Ser Gly Lys Leu Arg Met Lys Tyr Lys Phe
                85                  90                  95

Gln Asp Ala Tyr Asn Gln Lys Asp Leu Pro Ala Val Asn Ala Arg Arg
                100                 105                 110

Gln Ala Glu Phe Glu His Phe Gln Arg Arg Glu Gly Leu Pro Arg Pro
                115                 120                 125

Pro Pro Leu Leu Ala Pro Pro Asn Leu Pro Phe Gly Tyr Pro Val His
```

```
            130                 135                 140
Gly Val Glu Val Met Pro Leu His Thr Ile Leu Ile Pro Gly Leu Gln
145                 150                 155                 160

Tyr Glu Gly Pro Asp Ala Pro Val Tyr Glu Val Ile Leu Lys Ala Ser
                165                 170                 175

Leu Gly Thr Leu Asn Thr Leu Ala Asp Val Pro Asp Asp Glu Val Gln
            180                 185                 190

Gly Arg Gly Gln Arg Gln Leu Thr Ile Ser Thr Arg His Arg Lys Val
        195                 200                 205

Leu Asn Phe Ile Leu Gln His Val Thr Tyr Thr Ser Thr Glu Tyr Tyr
    210                 215                 220

Leu His Lys Val Asp Thr Val Ser Met Glu Tyr Glu Ser Ser Val Ala
225                 230                 235                 240

Lys Phe Pro Val Thr Ile Lys Gln Gln Thr Val Pro Lys Leu Tyr Asp
                245                 250                 255

Pro Gly Pro Glu Arg Lys Ile Arg Asn Leu Val Thr Ile Ala Thr Lys
            260                 265                 270

Thr Phe Leu Arg Pro His Lys Leu Lys Ile Leu Leu Gln Ser Ile Arg
        275                 280                 285

Lys Tyr Tyr Pro Asp Ile Thr Val Ile Val Ala Asp Asp Ser Lys Glu
    290                 295                 300

Pro Leu Glu Ile Asn Asp Asp Tyr Val Glu Tyr Tyr Thr Met Pro Phe
305                 310                 315                 320

Gly Lys Gly Trp Phe Ala Gly Arg Asn Leu Ala Ile Ser Gln Val Thr
                325                 330                 335

Thr Lys Tyr Val Leu Trp Val Asp Asp Asp Phe Leu Phe Ser Asp Lys
            340                 345                 350

Thr Lys Ile Glu Val Leu Val Asp Val Leu Glu Lys Thr Glu Leu Asp
        355                 360                 365

Val Val Gly Gly Ser Val Gln Gly Asn Thr Tyr Gln Phe Arg Leu Leu
    370                 375                 380

Tyr Glu Gln Thr Lys Asn Gly Ser Cys Leu His Gln Arg Trp Gly Ser
385                 390                 395                 400

Phe Gln Ala Leu Asp Gly Phe Pro Gly Cys Thr Leu Thr Ser Gly Val
                405                 410                 415

Val Asn Phe Phe Leu Ala His Thr Glu Gln Leu Arg Arg Val Gly Phe
            420                 425                 430

Asp Pro Ile Leu Gln Arg Val Ala His Gly Glu Phe Phe Ile Asp Gly
        435                 440                 445

Leu Gly Arg Leu Leu Val Gly Ser Cys Pro Gly Val Ile Ile Asn His
    450                 455                 460

Gln Val Arg Thr Pro Pro Lys Asp Pro Lys Leu Ala Ala Leu Glu Lys
465                 470                 475                 480

Thr Tyr Asp Lys Tyr Arg Ala Asn Thr Asn Ser Val Ile Gln Phe Lys
                485                 490                 495

Val Ala Leu Gln Tyr Phe Lys Asn His Leu Tyr Cys Ser Thr Asn
            500                 505                 510

<210> SEQ ID NO 4
<211> LENGTH: 1509
<212> TYPE: DNA
<213> ORGANISM: Sus scrofa

<400> SEQUENCE: 4
```

```
atgacttcgt acagccctag atgtctgtcg atcctcaaga tattgatggt gcttttggtc    60
ctgagcgttg gactctttat gttccaaagc gtgttcctcg atacagactt cagtctcctc   120
aactcaccca tcccgtcccc caccctggat gcgcagacgc taaagcttct acctgagaaa   180
cccgatttct acggtgaaaa cgggctgttc tcgaaaaacc agtgccaatg tgacgccttc   240
gggcatcagg aaagctataa cttggaggat gcctacgacc cgcaagacct ccccgcagtg   300
aacctgagga cacaggctga gctcgaacac tttcagagga gagaagggct ccctcgccca   360
ccgcccctgc tggctcagcc caacctcccc tttgggtacc cggtccacgg ggtggaagtg   420
atgcctctac acaccatccc catcccaggc ctccggtttg aaggacctga tgctcccatc   480
tatgaggtca ccctgacagc ttctctgggg acactgaacg cccttgctga cgtcccagac   540
aatgtggtga gggcagagg ccagaagcag ctgaacattt tgaccagtag ccgggagctt   600
ttgaatttca tcctccagca tgtgacatac acgagcacag agtaccacct ccacagagtg   660
gatgtggtga gtctggagtc caagtcctca gtggccaagt ttccagtgac catccgctat   720
cctgtcatgc ccaagttata tgaccctgga ccagagagga agctccgaga cctggtgacc   780
attgccacca aaaccttcct ccgtcccccac aagctcatga ccatgctccg gagtgttcgt   840
gagtactacc cagacctgac ggtgatcgtg gccgatgaca gcaaggagcc cctgaaaatc   900
actgacagcc acgtggagta ttacaccatg ccatttggga agggctggtt tgctggcagg   960
aacctggcca tatctcaggt caccaccaaa tatgtgctct gggtggacga tgacttcatc  1020
ttcaacagca agaccaggat cgaggcgctg gcggacgtcc tagagaaaac ggaactggac  1080
gtggtaggtg gcagcgtgat tgaaaacaca ttccagttca agctgttgct ggagcagggg  1140
aagaatggcg actgtctcca ccagcagcca ggatttttcc ggcccgtgga tggcttcccc  1200
gactgcgtgt tgaccagtgg tgttgtcagc ttcttcctgg ctcacacaga gcgactccaa  1260
agaattggct tcgaccccg gctgcagcga gtggctcact cagagttctt tattgatggg  1320
ctcgggagcc tgctcgtggg gtcctgccca cacgtgatca taggtcacca gccccattta  1380
ccagtgatgg acccagagct ggccaccctg aggggaact acaccagtta tcgggccaac  1440
accgaagccc agatcaaatt caagttggct ctccactact tcaagaacta tctccaatgt  1500
gccaccctaa                                                        1509
```

<210> SEQ ID NO 5  
<211> LENGTH: 798  
<212> TYPE: DNA  
<213> ORGANISM: Sus scrofa

<400> SEQUENCE: 5

```
gacagccacg tggagtatta cgccatgcca tttgggaagg tatattcctc ccagagggg    60
agacacgggc accctgggac cagagggccc cagggtcaag tggtaccctg gttgggctg   120
cttcggggtt gggggggacc ctctcacggc agcaggatcc ttgggggcg gagggtgggg   180
actcctctga gtcccctggc tgcctccaaa ttcccggaga atcaggtca ctctcccttt   240
cctgcagtga cggggtgggt aatccgtctt tcctcacgct tggtgtggaa attgatggag   300
gtccttgtaa gcgactggcg tgtctgacg ctctaaggtt tcctgatacg caggtcccac   360
agcagagaaa cctctctcat gatttcaccc ttgctgggc gtctctctcc gcgccccaca   420
ccttccctcg agcacaccgg gaggaagtgg atgttacccc ttccagagag cccccaccctc  480
cagcatcttc caggcaacac agggcgaaag ggccacaaag actgtcaggt gtaaagggac   540
ttgcatccat ccctcaagcc acacggccaa ggaaggactt tctcgtctcc agagagtccc   600
```

```
tctccttctt ccagggtctc tgagacatgg actcccttta gcccagaggt tttcagccac     660
tgtctggggg gcagcctgac ccttgggagc tgagaaagcc cccaggtgat gctaggaggc     720
agcggggcgg gcaaccacgg gtctaacctc cctgccctcg cagggctggt ttgctggcag     780
aaacctggcc atatctca                                                   798
```

<210> SEQ ID NO 6
<211> LENGTH: 907
<212> TYPE: DNA
<213> ORGANISM: Sus scrofa

<400> SEQUENCE: 6

```
gcgactccaa agaattggct tcgaccccccg gctgcagcga gtggctcact cacgtgggga    60
ggctggaagg gcaagaagcg agctgggctg tgcgctggct tcagaagtct ctttctgagg    120
gagggcgggg ccccactgct cagggaagcg gcccctttctc cccaaactag ggagctcttg   180
gtctctcttg cctccctcca ccttcgtgtc tcccataggc tattcctgct ctccgagac     240 acccttctac ctcctctccc tgcagctctg ccccttccct cttttccttgt cttgctgctg   300 ctcctccttt tttttgcctt tgtagggctg cacccatggc atgtggaggt tcccaggcta    360
ggggttgaat tggagctttt gctcccggcc tatgccagag ccacagcaac acgggatctg    420
agctgcttct gtgacctaca ccacagctca gggcagcgcc agatccttaa cccactgaac   480
gaggccaggg accgaaccca caacctcatg gttcctagtc ggattcatta accactacgc    540
catgaccgga atttcctgct cctccttttc cagacatcct tctctgttta gctgcagctg    600
gtgagcagca ccccacctct tccctctca ttcctcccag tcctggggtc tactaatctg    660
tgtctctctg ctgatatctg tctgatcttc caactcagtg gctttgccat gggactgaac    720
ctccccagaa tagaagctat ttccccccgc cccagccctc ctcccagagt cgcagtattg    780
gcccgggtct ctggtttgaa gctcacgttt ccttctcgcg ctctctccct ctcttggcag    840
agttctttat tgatgggctc gggagcctgc tcgtggggtc ctgcccacac gtgatcatag    900
gtcacca                                                              907
```

<210> SEQ ID NO 7
<211> LENGTH: 15
<212> TYPE: PRT
<213> ORGANISM: Homo sapiens

<400> SEQUENCE: 7

```
Ser Gln Val Thr Thr Lys Tyr Val Leu Trp Val Asp Asp Asp Phe
1               5                   10                  15
```

<210> SEQ ID NO 8
<211> LENGTH: 12
<212> TYPE: DNA
<213> ORGANISM: Sus scrofa

<400> SEQUENCE: 8

```
atgacttcgt ac                                                         12
```

<210> SEQ ID NO 9
<211> LENGTH: 12
<212> TYPE: DNA
<213> ORGANISM: Sus scrofa

<400> SEQUENCE: 9

```
aggtgagtgt cc                                                         12
```

<210> SEQ ID NO 10
<211> LENGTH: 12
<212> TYPE: DNA
<213> ORGANISM: Sus scrofa

<400> SEQUENCE: 10
ttgtgtccca ac                                                          12

<210> SEQ ID NO 11
<211> LENGTH: 12
<212> TYPE: DNA
<213> ORGANISM: Sus scrofa

<400> SEQUENCE: 11
agccctagat gt                                                          12

<210> SEQ ID NO 12
<211> LENGTH: 12
<212> TYPE: DNA
<213> ORGANISM: Sus scrofa

<400> SEQUENCE: 12
ggtgaaaacg gg                                                          12

<210> SEQ ID NO 13
<211> LENGTH: 12
<212> TYPE: DNA
<213> ORGANISM: Sus scrofa

<400> SEQUENCE: 13
tgagatggca ag                                                          12

<210> SEQ ID NO 14
<211> LENGTH: 12
<212> TYPE: DNA
<213> ORGANISM: Sus scrofa

<400> SEQUENCE: 14
tcttatttta gg                                                          12

<210> SEQ ID NO 15
<211> LENGTH: 12
<212> TYPE: DNA
<213> ORGANISM: Sus scrofa

<400> SEQUENCE: 15
ctgttcccga aa                                                          12

<210> SEQ ID NO 16
<211> LENGTH: 12
<212> TYPE: DNA
<213> ORGANISM: Sus scrofa

<400> SEQUENCE: 16
ctttcagagg ag                                                          12

<210> SEQ ID NO 17
<211> LENGTH: 12
<212> TYPE: DNA
<213> ORGANISM: Sus scrofa

<400> SEQUENCE: 17

-continued gtattgcaga tg                                                          12

<210> SEQ ID NO 18
<211> LENGTH: 12
<212> TYPE: DNA
<213> ORGANISM: Sus scrofa

<400> SEQUENCE: 18
gtttccctgc ag                                                          12

<210> SEQ ID NO 19
<211> LENGTH: 12
<212> TYPE: DNA
<213> ORGANISM: Sus scrofa

<400> SEQUENCE: 19
agaagggctc cc                                                          12

<210> SEQ ID NO 20
<211> LENGTH: 12
<212> TYPE: DNA
<213> ORGANISM: Sus scrofa

<400> SEQUENCE: 20
ccccatccca gg                                                          12

<210> SEQ ID NO 21
<211> LENGTH: 12
<212> TYPE: DNA
<213> ORGANISM: Sus scrofa

<400> SEQUENCE: 21
taggtgcatc tc                                                          12

<210> SEQ ID NO 22
<211> LENGTH: 12
<212> TYPE: DNA
<213> ORGANISM: Sus scrofa

<400> SEQUENCE: 22
gtgacctcca gg                                                          12

<210> SEQ ID NO 23
<211> LENGTH: 12
<212> TYPE: DNA
<213> ORGANISM: Sus scrofa

<400> SEQUENCE: 23
cctccggttt ga                                                          12

<210> SEQ ID NO 24
<211> LENGTH: 12
<212> TYPE: DNA
<213> ORGANISM: Sus scrofa

<400> SEQUENCE: 24
cccatctatg ag                                                          12

<210> SEQ ID NO 25
<211> LENGTH: 12
<212> TYPE: DNA
<213> ORGANISM: Sus scrofa

<400> SEQUENCE: 25

-continued

```
gcaagagtcc cc                                                           12

<210> SEQ ID NO 26
<211> LENGTH: 12
<212> TYPE: DNA
<213> ORGANISM: Sus scrofa

<400> SEQUENCE: 26
cctttatcct ag                                                           12

<210> SEQ ID NO 27
<211> LENGTH: 12
<212> TYPE: DNA
<213> ORGANISM: Sus scrofa

<400> SEQUENCE: 27
gtcaccctga ca                                                           12

<210> SEQ ID NO 28
<211> LENGTH: 12
<212> TYPE: DNA
<213> ORGANISM: Sus scrofa

<400> SEQUENCE: 28
agagtggatg tg                                                           12

<210> SEQ ID NO 29
<211> LENGTH: 12
<212> TYPE: DNA
<213> ORGANISM: Sus scrofa

<400> SEQUENCE: 29
ggtgagtccg tc                                                           12

<210> SEQ ID NO 30
<211> LENGTH: 12
<212> TYPE: DNA
<213> ORGANISM: Sus scrofa

<400> SEQUENCE: 30
tttctccctc ca                                                           12

<210> SEQ ID NO 31
<211> LENGTH: 12
<212> TYPE: DNA
<213> ORGANISM: Sus scrofa

<400> SEQUENCE: 31
gtgagtctgg ag                                                           12

<210> SEQ ID NO 32
<211> LENGTH: 12
<212> TYPE: DNA
<213> ORGANISM: Sus scrofa

<400> SEQUENCE: 32
gaccctggac ca                                                           12

<210> SEQ ID NO 33
<211> LENGTH: 12
<212> TYPE: DNA
<213> ORGANISM: Sus scrofa
```

-continued

<400> SEQUENCE: 33
ggtaagaccc ct							12

<210> SEQ ID NO 34
<211> LENGTH: 12
<212> TYPE: DNA
<213> ORGANISM: Sus scrofa

<400> SEQUENCE: 34
ctttcttgcc ca							12

<210> SEQ ID NO 35
<211> LENGTH: 12
<212> TYPE: DNA
<213> ORGANISM: Sus scrofa

<400> SEQUENCE: 35
gagaggaagc tc							12

<210> SEQ ID NO 36
<211> LENGTH: 12
<212> TYPE: DNA
<213> ORGANISM: Sus scrofa

<400> SEQUENCE: 36
ccatttggga ag							12

<210> SEQ ID NO 37
<211> LENGTH: 12
<212> TYPE: DNA
<213> ORGANISM: Sus scrofa

<400> SEQUENCE: 37
gtatattcct cc							12

<210> SEQ ID NO 38
<211> LENGTH: 12
<212> TYPE: DNA
<213> ORGANISM: Sus scrofa

<400> SEQUENCE: 38
ctgccctcgc ag							12

<210> SEQ ID NO 39
<211> LENGTH: 12
<212> TYPE: DNA
<213> ORGANISM: Sus scrofa

<400> SEQUENCE: 39
ggctggtttg ct							12

<210> SEQ ID NO 40
<211> LENGTH: 12
<212> TYPE: DNA
<213> ORGANISM: Sus scrofa

<400> SEQUENCE: 40
gaactggacg tg							12

<210> SEQ ID NO 41
<211> LENGTH: 12
<212> TYPE: DNA
<213> ORGANISM: Sus scrofa

```
<400> SEQUENCE: 41
gtaagtgagc tg                                                              12

<210> SEQ ID NO 42
<211> LENGTH: 12
<212> TYPE: DNA
<213> ORGANISM: Sus scrofa

<400> SEQUENCE: 42
cccgctggct ag                                                              12

<210> SEQ ID NO 43
<211> LENGTH: 12
<212> TYPE: DNA
<213> ORGANISM: Sus scrofa

<400> SEQUENCE: 43
gtaggtggca gc                                                              12

<210> SEQ ID NO 44
<211> LENGTH: 12
<212> TYPE: DNA
<213> ORGANISM: Sus scrofa

<400> SEQUENCE: 44
gtggctcact ca                                                              12

<210> SEQ ID NO 45
<211> LENGTH: 12
<212> TYPE: DNA
<213> ORGANISM: Sus scrofa

<400> SEQUENCE: 45 cgtgggagg ct                                                               12

<210> SEQ ID NO 46
<211> LENGTH: 12
<212> TYPE: DNA
<213> ORGANISM: Sus scrofa

<400> SEQUENCE: 46
cctctcttgg ca                                                              12

<210> SEQ ID NO 47
<211> LENGTH: 12
<212> TYPE: DNA
<213> ORGANISM: Sus scrofa

<400> SEQUENCE: 47 gagttctta tt                                                               12
```